(12) United States Patent
Yamada et al.

(10) Patent No.: US 9,969,931 B2
(45) Date of Patent: May 15, 2018

(54) ELECTROCHROMIC COMPOSITION AND ELECTROCHROMIC ELEMENT

(71) Applicant: CANON KABUSHIKI KAISHA, Tokyo (JP)

(72) Inventors: Kenji Yamada, Yokohama (JP); Shinjiro Okada, Kamakura (JP); Jun Yamamoto, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days. days.

(21) Appl. No.: 15/317,372

(22) PCT Filed: Jun. 30, 2015

(86) PCT No.: PCT/JP2015/003296
§ 371 (c)(1),
(2) Date: Dec. 8, 2016

(87) PCT Pub. No.: WO2016/006204
PCT Pub. Date: Jan. 14, 2016

(65) Prior Publication Data
US 2017/0114274 A1    Apr. 27, 2017

(30) Foreign Application Priority Data

Jul. 11, 2014    (JP) .................. 2014-143666

(51) Int. Cl.
*G02F 1/153*    (2006.01)
*G02F 1/15*    (2006.01)
(Continued)

(52) U.S. Cl.
CPC .............. *C09K 9/02* (2013.01); *C07D 333/16* (2013.01); *G02F 1/15* (2013.01); *G02F 1/155* (2013.01);
(Continued)

(58) Field of Classification Search
CPC .. C09K 9/02; C09K 11/06; C09K 2211/1044; C09K 2211/1092; C07D 333/16;
(Continued)

(56) References Cited

U.S. PATENT DOCUMENTS 5,290,930 A    3/1994   Byker
5,910,854 A *  6/1999   Varaprasad ............. B32B 17/06
                                                                 359/273

(Continued)

FOREIGN PATENT DOCUMENTS

JP    H11271814 A    10/1999
JP    2008096786     4/2008
(Continued)

OTHER PUBLICATIONS

J. Guay, et al., Chain-Length Dependence of Electrochemical and Electronic Properties of Neutral and Oxidized Soluble α,α-Coupled Thiophene Oligomers, Chemistry of Materials. 1992, pp. 1097-1105, vol. 4, No. 5.
(Continued)

*Primary Examiner* — Loha Ben
(74) *Attorney, Agent, or Firm* — Canon U.S.A., Inc. IP Division

(57) ABSTRACT

An electrochromic composition has an anodic electrochromic compound and a cathodic electrochromic compound, in
(Continued)

which the anodic electrochromic compound is represented by General Formula [1]

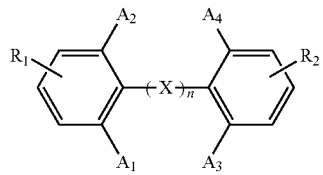

and the cathodic electrochromic compound is represented by General Formula [2]

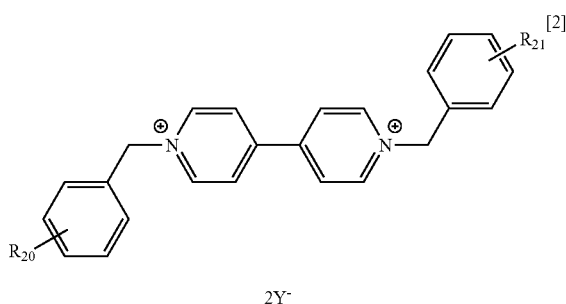

In General Formula 1, $A_1$ to $A_4$ represent substituents, $R_1$ and $R_2$, and $R_{20}$ and $R_{21}$ represent a hydrogen atom or a substituent. n is an integer of 1 to 5. X represents a thiophene derivative and Y- represents an anion.

16 Claims, 7 Drawing Sheets

(51) Int. Cl.
  *C09K 9/00* (2006.01)
  *C09K 9/02* (2006.01)
  *C07D 333/16* (2006.01)
  *G02F 1/157* (2006.01)
  *G02F 1/155* (2006.01)
  *H04N 5/225* (2006.01)
(52) U.S. Cl.
  CPC ........... *G02F 1/157* (2013.01); *H04N 5/2253* (2013.01); *H04N 5/2254* (2013.01); *C09K 2211/1044* (2013.01); *C09K 2211/1092* (2013.01); *G02F 1/1521* (2013.01); *G02F 2001/1512* (2013.01); *G02F 2001/1515* (2013.01)
(58) Field of Classification Search
  CPC ...... H04N 5/2253; H04N 5/2254; G02F 1/15; G02F 1/155; G02F 1/157; G02F 1/153; G02F 1/1521; G02F 2001/1512; G02F 2001/1515
  USPC ....... 359/265, 270, 273, 275, 823, 694–696; 252/582, 583, 586
  See application file for complete search history.

(56) References Cited

U.S. PATENT DOCUMENTS

| | | | |
|---|---|---|---|
| 7,428,091 B2* | 9/2008 | Baumann | C09K 11/02 359/265 |
| 7,450,292 B1* | 11/2008 | Burrell | B60R 1/088 252/583 |
| 7,855,821 B2* | 12/2010 | Baumann | C09K 11/06 252/582 |
| 9,738,140 B2* | 8/2017 | Ash | G02F 1/15 |

FOREIGN PATENT DOCUMENTS

| | | |
|---|---|---|
| JP | 2009086259 A | 4/2009 |
| JP | 2013133329 A | 7/2013 |
| JP | 2014073996 A | 4/2014 |
| WO | 2006/055391 A2 | 5/2006 |
| WO | 2013/099523 A1 | 7/2013 |

OTHER PUBLICATIONS

Corwin Hansch, et al., A Survey of Hammett Substituent Constants and Resonance and Field Parameters, Chemical Reviews, 1991, pp. 165-195, vol. 91, No. 2.

* cited by examiner

[Chem.1]

[1]

[Chem.2]

[2]

ELECTROCHROMIC COMPOSITION AND ELECTROCHROMIC ELEMENT

CROSS-REFERENCE TO RELATED APPLICATIONS

This application is a National Stage filing of International Application No. PCT/JP2015/003296 filed Jun. 30, 2015, which claims the benefit of Japanese Patent Application No. 2014-143666, filed Jul. 11, 2014, the disclosures of each of which are hereby incorporated by reference herein in their entirety.

TECHNICAL FIELD

The present invention relates to an electrochromic composition, an electrochromic element, an optical filter, a lens unit, and an imaging device.

BACKGROUND ART

Various materials have been reported as an electrochromic (which is sometimes abbreviated as "EC" below) material in which the light absorption properties (coloration state and light transmittance) of a substance change due to an electrochemical redox reaction. Those containing metal oxides, such as $WO_3$, have been known as inorganic EC materials but a forming method is limited to a vapor deposition method and the like, which has caused a problem in producing a large area device.

On the other hand, as organic EC materials, conductive polymers, such as polythiophene and polyaniline, organic low molecular weight compounds, such as viologen and oligothiophene, and the like have been known. Herein, examples of the organic low molecular weight EC compounds include viologen derivatives and quinone derivatives which are cathodic compounds which are colored by reduction, oligothiophene derivatives and phenazine derivatives which are anodic compounds which are colored by oxidation, and the like.

The organic low molecule weight EC compounds have been known to have higher transparency in decoloration as compared with conductive polymer EC compounds.

PTL 1 describes a phenazine derivative as the anodic EC compound which is colored in an oxidized state. PTL 2 describes a viologen derivative as the cathodic EC compound. NPL 1 describes an oligothiophene derivative as the anodic EC compound. PTL 3 describes a dithienothiophene derivative as an anode material.

As an EC element containing the organic low molecule weight EC compound, a so-called sandwich type complementary element in which a solution obtained by dissolving an anodic EC compound and a cathodic EC compound is disposed between a pair of electrodes has been known.

Since the anodic EC compound has abundant electrons in the molecules, the anodic EC compound is easily oxidized. As a result, the anodic EC compound has an electron donor property. On the other hand, since electrons are insufficient in the molecules in the cathodic EC compound, the cathodic EC compound is easily reduced. As a result, the cathodic EC compound has an electron acceptor property. Therefore, when both the EC compounds are mixed and dissolved, electron donor molecules and electron acceptor molecules interact to form a charge transfer (CT) complex, and then light absorption based on the charge transfer complex appears in a visible region. Even in the case where the anodic EC compound and the cathodic EC compound each individually have sufficient colorless transparency in decoloration, when the anodic EC compound and the cathodic EC compound are mixed, a problem that CT absorption appears in a visible region and the transparency decreases has occurred.

PTL 1 describes that the CT light absorption can be reduced in a solution containing viologen by a 5,10-dihydrophenazine derivative of a specific structure which is the anodic EC compound.

CITATION LIST

Patent Literature

PTL 1: International Publication No. WO2006/055391
PTL 2: U.S. Pat. No. 5,290,930
PTL 3: International Publication No. WO2013/099523

Non Patent Literature

NPL 1: GUAY, J; KASAI, P; DIAZ, A et al. "CHAIN-LENGTH DEPENDENCE OF ELECTROCHEMICAL AND ELECTRONIC-PROPERTIES OF NEUTRAL AND OXIDIZED SOLUBLE ALPHA, ALPHA-COUPLED THIOPHENE OLIGOMERS" Chemistry of Materials. 1992, Volume 4. No. 5, 1097-1105

NPL 2: Corwin Hansch et al, "A Survey of Hammett Substituent Constants and Resonace and Field Parameters" Chemical Reviews, Volume 91, 165 to 195, 1991

SUMMARY OF INVENTION

The present invention provides an EC composition which suppresses CT interaction when mixing both an anodic EC compound and a cathodic EC compound by controlling the molecular structure of the anodic EC compound and the cathodic EC compound and can maintain sufficiently high colorless transparency in decoloration.

Then, the present invention provides an electrochromic composition having an anodic electrochromic compound and a cathodic electrochromic compound, in which the anodic electrochromic compound is represented by the following general formula [1] and the cathodic electrochromic compound is represented by the following general formula [2].

[Chem. 1]

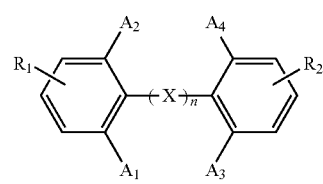

[1]

-continued

[Chem. 2]

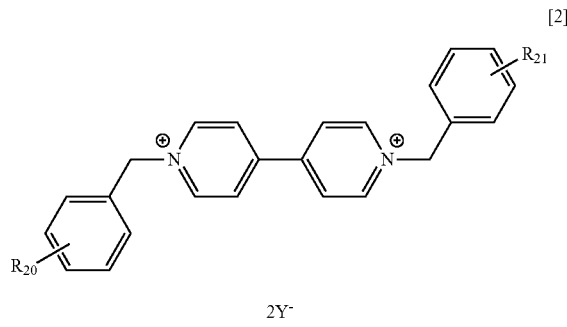

[2]

-continued

[Chem. 4]

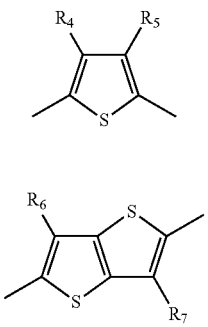

[4]

[Chem. 5]

[5]

In General Formula [1], A1 to A4 each independently represent a substituent selected from alkyl groups in which the number of carbon atoms is 1 or more and 20 or less, alkoxy groups in which the number of carbon atoms is 1 or more and 20 or less, and aryl groups which may have a substituent.

When the aryl group has a substituent, the substituent is at least any one of alkyl groups in which the number of carbon atoms is 1 or more and 8 or less or alkoxy groups in which the number of carbon atoms is 1 or more and 8 or less.

R1 and R2 each are independently selected from hydrogen atoms or substituents. The substituents represented by R1 and R2 above each are at least any one of halogen atoms, alkyl groups in which the number of carbon atoms is 1 or more and 20 or less, alkoxy groups in which the number of carbon atoms is 1 or more and 20 or less, alkyl ester groups in which the number of carbon atoms is 1 or more and 20 or less, aryl groups which may have a substituent, amino groups which may have a substituent, or cyano groups. Two or more R1s and R2s may be present.

n is an integer of 1 to 5.

In General Formula [2], R20 and R21 each are independently selected from hydrogen atoms or substituents. The substituents represented by R20 and R21 above each are at least any one selected from halogen atoms, alkyl groups in which the number of carbon atoms is 1 or more and 20 or less, alkoxy groups in which the number of carbon atoms is 1 or more and 20 or less, alkyl ester groups in which the number of carbon atoms is 1 or more and 20 or less, acyl groups in which the number of carbon atoms is 1 or more and 20 or less, aryl groups which may have a substituent, amino groups which may have a substituent, or cyano groups. Two or more R20s and R21 s may be present. Y⁻ represents an anion.

X is the structure having any one of the following general formulae [3] to [5], in which when n is 2 or more, a plurality of Xs each are independently selected from the following general formula [3] to [5].

[Chem. 3]

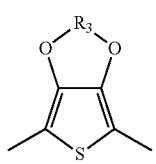

[3]

In General Formula [3], R3 represents an alkylene group in which the number of carbon atoms is 1 or more and 20 or less and which may be branched.

In General Formula [4]. R4 to R7 each represent a hydrogen atom or a substituent. The substituents represented by R4 to R7 above each are at least any one of halogen atoms, alkyl groups in which the number of carbon atoms is 1 or more and 20 or less, alkoxy groups in which the number of carbon atoms is 1 or more and 20 or less, aryl groups which may have a substituent, alkyl ester groups in which the number of carbon atoms is 1 or more and 20 or less, amino groups which may have a substituent, or cyano groups.

Further features of the present invention will become apparent from the following description of exemplary embodiments with reference to the attached drawings.

DESCRIPTION OF EMBODIMENT

Figure 1A:
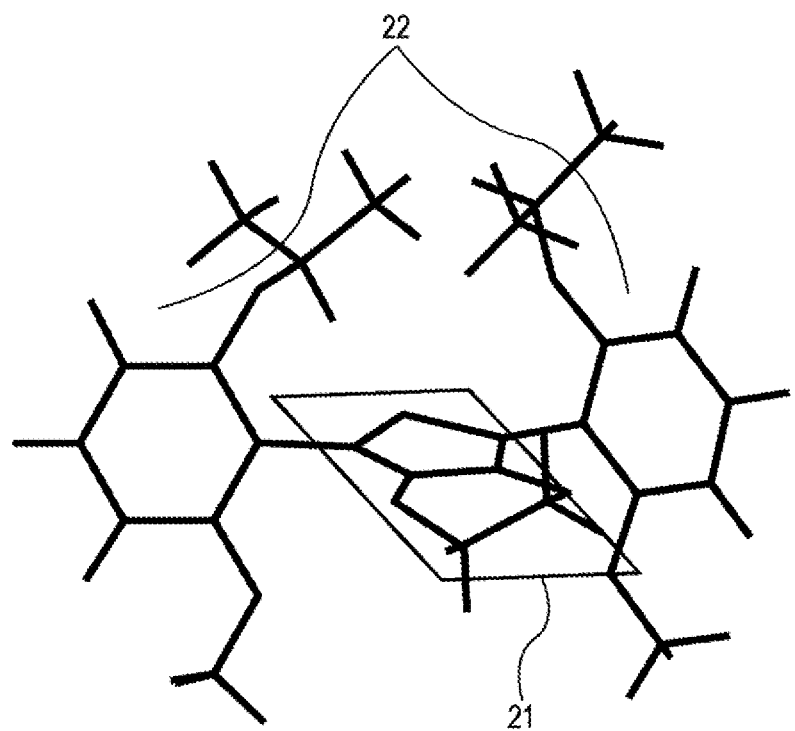
FIG. 1A is a view showing an example of an anodic EC compound configuring an EC composition according to an aspect of the present invention in the molecular model.

Hereinafter, an embodiment of the present invention is described in detail.

The present invention relates to an EC composition having an anodic EC compound and a cathodic EC compound. Since the anodic EC compound and the cathodic EC compound are compounds represented by General Formula [1] and General Formula [2], respectively, CT light absorption can be suppressed.

Anodic Electrochromic Compound

First, an anodic electrochromic compound (anodic EC compound) configuring an EC composition according to an aspect of the present invention is described. The anodic EC compound in an aspect of the present invention is a compound in which the transmittance of visible light in an oxidized state is lower than the transmittance of visible light in a reduced state. The anodic EC compound is a compound represented by General Formula [1].

[Chem. 6]

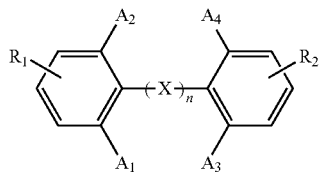

[1]

The anodic EC compound has a thiophene derivative represented by X in General Formula [1] and a phenyl group bonded thereto.

In Formula [1], A1 to A4 each independently represent a substituent selected from alkyl groups in which the number of carbon atoms is 1 or more and 20 or less, alkoxy groups in which the number of carbon atoms is 1 or more and 20 or less, and aryl groups which may have a substituent. In the present invention, it is suitable that A1 and A3 represent the same substituent and A2 and A4 represent the same substituent.

The alkyl groups represented by A1 to A4 may have a straight chain shape, a branched chain shape, or a cyclic shape. The alkyl groups represented by A1 to A4 are suitably alkyl groups in which the number of carbon atoms is 1 or more and 6 or less.

Examples of the alkyl groups represented by A1 to A4 include, for example, a methyl group, an ethyl group, a normal propyl group, an isopropyl group, a normal butyl group, a tertiary butyl group, a pentyl group, a hexyl group, an octyl group, a dodecyl group, a cyclohexyl group, a bicyclo octyl group, an adamantyl group, and the like. At least one part of the hydrogen atom contained in the alkyl group may be substituted with a fluorine atom to be a trifluoromethyl group or the like, for example.

The alkyl groups represented by A1 to A4 are suitably a methyl group, an ethyl group, a normal butyl group, or a hexyl group and more suitably a methyl group or an ethyl group.

The alkoxy groups represented by A1 to A4 may have a straight chain shape, a branched chain shape, or a cyclic shape. The alkoxy groups represented by A1 to A4 are suitably alkoxy groups in which the number of carbon atoms is 1 or more and 8 or less.

Examples of the alkoxy groups represented by A1 to A4 include a methoxy group, an ethoxy group, an isopropoxy group, an n-butoxy group, a tert-butoxy group, an ethylhexyloxy group, an octyloxy group, a benzyloxy group, and the like, for example.

At least either one of A1 or A2 is suitably an alkoxy group. At least either one of A3 or A4 is suitably alkoxy.

Among the alkoxy groups mentioned above, a methoxy group, an ethoxy group, or an isopropoxy group is suitable and a methoxy group or an isopropoxy group is more suitable.

Examples of the aryl groups represented by A1 to A4 include a phenyl group, a biphenyl group, a fluorenyl group, a naphthyl group, a fluoranthenyl group, an anthryl group, a phenanthryl group, a pyrenyl group, a perylenyl group, and the like, for example. A phenyl group is suitable.

When any one of A1 to A4 is an aryl group, the aryl group may further have an alkyl group in which the number of carbon atoms is 1 or more and 8 or less, an alkoxy group in which the number of carbon atoms is 1 or more and 8 or less, an aryl group, an aralkyl group, a substituted amino group, or a substituted silyl group, and specifically, a phenyl group, a biphenyl group, a naphthyl group, a benzyl group, a dimethylamino group, a triisopropylsilyl group, or the like. The alkyl group contained as a substituent in the aryl group is suitably an alkyl group in which the number of carbon atoms is 1 or more and 4 or less. The alkoxy group contained as a substituent in the aryl group is suitably an alkoxy group in which the number of carbon atoms is 1 or more and 4 or less.

R1 and R2 each are independently selected from hydrogen atoms or substituents. The substituents represented by R1 and R2 each are at least any one of halogen atoms, alkyl groups in which the number of carbon atoms is 1 or more and 20 or less, alkoxy groups in which the number of carbon atoms is 1 or more and 20 or less, alkylester groups in which the number of carbon atoms is 1 or more and 20 or less, aryl groups which may have a substituent, amino groups which may have a substituent, or cyano groups.

The aryl group may have an alkyl group in which the number of carbon atoms is 1 or more and 4 or less as a substituent. When R1 and R2 are substituents, the number of R1 and R2 substituted with one aromatic ring may be one or two or more. More specifically, two or more R1s and R2s may be present.

Among these substituents, since an electron donating substituent is suitable because the electron donating substituent has an effect of increasing the electron density in the thiophene part represented by X. The oxidation potential decreases due to electron donating of the substituent, which produces an effect of reducing a drive voltage when configuring an EC element and an effect of increasing the stability of radical cation generated by oxidation.

Therefore, as the substituents represented by R1 and R2, a methyl group, an ethyl group, a methoxy group, an isopropoxy group, and a dimethylamino group are particularly suitable. This is because these substituents have high electron donating property.

Among the substituents represented by R1 and R2, polar substituents, such as an alkoxy group and an alkyl ester group, can increase the solubility in a polar solvent. Therefore, the polar substituents are suitably used for an EC element in which an electrochromic layer is a solution layer.

This is because, by dissolving a high concentration of an EC material in the EC layer, the contrast in coloring can be increased. In this viewpoint, as the substituents represented by R1 and R2, a methyl ester group, an isopropyl ester group, a tertbutylester group, a methoxy group, and an isopropoxy group are particularly suitable.

X in General Formula [1] is a thiophene derivative represented by any one of General Formulae [3] to [5]. n in General Formula [1] represents an integer of 1 to 5. When n is 2 or more, a plurality of Xs may be the same or different from each other. The thiophene derivative is a compound which shows the EC property in which the thiophene derivative is colored when oxidized.

[Chem. 7]

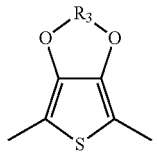

[3]

[Chem. 8]

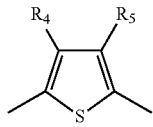

[4]

[Chem. 9]

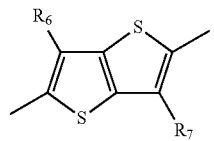

[5]

In General Formulae [3] to [5], the bond in which R is not indicated represents a portion to be bonded to the phenyl group shown in General Formula [1].

In General Formula [3], the alkylene group represented by R3 is an alkylene group in which the number of carbon atoms is 1 or more and 20 or less and which may be branched. R3 is suitably an alkylene group in which the number of carbon atoms is 1 or more and 4 or less.

Specifically, a methylene group, an ethylene group, an n-propylene group, an n-butylene group, an isopropylene group, an isobutylene group, and the like are mentioned, for example.

In General Formulae [4] and [5], R4 to R7 each are independently selected from hydrogen atoms or substituents. The substituents each represented by R4 to R7 are at least one of a halogen atom, an alkyl group in which the number of carbon atoms is 1 or more and 20 or less, an alkoxy group in which the number of carbon atoms is 1 or more and 20 or less, an aryl group which may have a substituent, an alkylester group in which the number of carbon atoms is 1 or more and 20 or less, an amino group which may have a substituent, or a cyano group.

The alkyl groups in which the number of carbon atoms is 1 or more and 20 or less represented by R4 to R7 may have a straight chain shape, a branched chain shape, or a cyclic shape. This alkyl group is suitably an alkyl group in which the number of carbon atoms is 1 or more and 6 or less and more suitably an alkyl group in which the number of carbon atoms is 1 or 2.

Specifically, a methyl group, an ethyl group, a normal propyl group, an isopropyl group, a normal butyl group, a tertiary butyl group, a pentyl group, a hexyl group, an octyl group, a dodecyl group, a cyclohexyl group, a bicyclooctyl group, an adamantyl group, and the like are mentioned, for example. A hydrogen atom in an alkyl group may be substituted with a fluorine atom and, for example, a trifluoromethyl group or the like may be formed.

Among the above, a methyl group, an ethyl group, a normal butyl group, or a hexyl group is suitable and a methyl group or an ethyl group is more suitable.

The alkoxy groups in which the number of carbon atoms is 1 or more and 20 or less represented by R4 to R7 may have a straight chain shape, a branched chain shape, or a cyclic shape. In the alkoxy group, the number of carbon atoms is suitably 1 or more and 8 or less.

Specifically, a methoxy group, an ethoxy group, an isopropoxy group, an n-butoxy group, a tert-butoxy group, an ethylhexyloxy group, an octyloxy group, and the like are mentioned, for example.

Examples of the aryl groups represented by R4 to R7 include a phenyl group, a biphenyl group, a fluorenyl group, a naphthyl group, a fluoranthenyl group, an anthryl group, and the like. A phenyl group is suitable.

The aryl groups represented by R4 to R7 may have an alkyl group in which the number of carbon atoms is 1 or more and 8 or less or an alkoxy group in which the number of carbon atoms is 1 or more and 8 or less as a substituent.

Examples of the alkyl ester groups in which the number of carbon atoms is 1 or more and 20 or less represented by R4 to R7 include a methyl ester group, an ethyl ester group, an n-propyl ester group, an isopropyl ester group, an n-butyl ester group, a tert-butyl ester group, a tert-amyl ester group, a hexyl ester group, a heptyl ester group, an octyl ester group, an ethylhexyl ester group, a cyclopentyl ester group, a cyclohexyl ester group, and the like.

Cathodic Electrochromic Compound

Next, the cathodic electrochromic compound (cathodic EC compound) configuring the EC composition according to an aspect of the present invention is described. The cathodic EC compound in an aspect of the present invention is a compound in which the transmittance of visible light in a reduced state is lower than the transmittance of visible light in an oxidized state. The cathodic EC compound is a compound represented by the following general formula [2].

[Chem. 10]

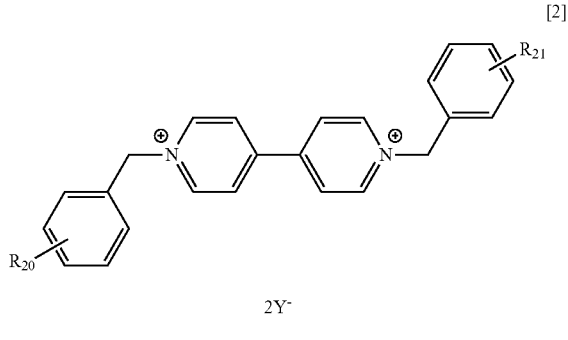

[2]

The compound represented by General Formula [2] has a 4,4'-bipyridinium salt (viologen) which is the EC part and a benzyl group which may have a substituent bonded thereto.

In General Formula [2], R20 and R21 each are independently selected from hydrogen atoms or substituents. The substituents each represented by R20 and R21 are at least one of a halogen atom, an alkyl group in which the number of carbon atoms is 1 or more and 20 or less, an alkoxy group in which the number of carbon atoms is 1 or more and 20 or less, an alkylester group in which the number of carbon atoms is 1 or more and 20 or less, an acyl group in which the number of carbon atoms is 1 or more and 20 or less, an aryl group which may have a substituent, an amino group which may have a substituent, or a cyano group. When R20 and R21 are substituents, the number of R20 and R21 substituted with one aromatic ring may be one or two or more. $Y^-$ represents an anion.

The alkyl groups represented by R20 and R21 may have a straight chain shape, a branched chain shape, or a cyclic shape. The alkyl groups represented by R20 and R21 are suitably alkyl groups in which the number of carbon atoms is 1 or more and 10 or less.

Examples of the alkyl groups represented by R20 and R21 include a methyl group, an ethyl group, a normal propyl group, an isopropyl group, a normal butyl group, a tert-butyl group, a pentyl group, a hexyl group, an octyl group, a dodecyl group, a cyclohexyl group, an adamantyl group, and the like, for example. At least one part of the hydrogen atom contained in the alkyl group may be substituted with a fluorine atom and a trifluoromethyl group or the like may be formed, for example.

The alkyl groups represented by R20 and R21 are suitably a methyl group, an isopropyl group, a tert-butyl group, or a trifluoromethyl group and more suitably a tert-butyl group or a trifluoromethyl group.

The alkoxy groups represented by R20 and R21 may have a straight chain shape, a branched chain shape, or a cyclic shape. The alkoxy groups represented by R20 and R21 are suitably alkoxy groups in which the number of carbon atoms is 1 or more and 10 or less.

Examples of the alkoxy groups represented by R20 and R21 include a methoxy group, an ethoxy group, an iso-propoxy group, an n-butoxy group, a tert-butoxy group, an ethylhexyloxy group, an octyloxy group, a benzyloxy group, and the like, for example.

Among the alkoxy groups, a methoxy group, a tert-butoxy group, or a benzyloxy group is suitable and a methoxy group or a benzyloxy group is more suitable.

The alkyl ester groups represented by R20 and R21 may have a straight chain shape, a branched chain shape, or a cyclic shape. The alkyl ester groups represented by R20 and R21 are suitably alkyl ester groups in which the number of carbon atoms is 1 or more and 10 or less.

Examples of the alkyl ester groups represented by R20 and R21 include a methyl ester group, an ethyl ester group, an isopropyl ester group, an n-butyl ester group, a tert-butyl ester group, an ethyl hexyl ester group, and the like, for example.

Among the alkyl ester groups, a methyl ester group and a tert-butyl ester group are suitable.

Examples of the acyl group in which the number of carbon atoms is 1 or more and 20 or less include an acetyl group, a propionyl group, a butyryl group, or a valenyl group, for example, and an acetyl group is particularly suitable.

Examples of the aryl groups represented by R20 and R21 include a phenyl group, a biphenyl group, a fluorenyl group, a naphthyl group, a fluoranthenyl group, an anthryl group, a phenanthryl group, a pyrenyl group, a perylenyl group, and the like, for example. A phenyl group is suitable.

Among these substituents, an electron withdrawing substituent is suitable. Herein, in the present invention, the electron withdrawing substituent is a substituent in which the Hammett op value described below is a positive value. The Hammett op value is a substituent constant determined from an electronic effect of a substituent exerted on the acid dissociation equilibrium constant of substituted benzoic acid by Hammett et al and a group described in NPL 2 can be quoted.

The electron withdrawing substituent in which the Hammett op value is a positive value has effects of reducing the electron density of the viologen part and reducing a drive voltage when configuring an EC element. Therefore, the substituents represented by R20 and R21 are particularly suitably a trifluoromethyl group, a methyl ester group, an acetyl group, and a cyano group. This is because these substituents have high electron withdrawing property.

Examples of the anion represented by $Y^-$ include anions, such as $PF_6^-$, $ClO_4^-$, $BF_4^-$, $AsFE_6^-$, $SbF_6^-$, $CF_3SO_3^-$, and $(CF_3SO_2)_2N^-$ and halogen anions, such as $Br^-$, $Cl^-$, and $I^-$. $Y^-$ is suitably any one of $PF_6^-$, $ClO_4^-$, $BF_4^-$, and $(CF_3SO_2)_2N^-$.

EC Composition Containing Anodic EC Compound and Cathodic EC Compound

By reducing electronic interaction which occurs between the molecules of the anodic EC compound and the cathodic EC compound due to the effect of steric hindrance of the substituents contained in the anodic compound and the cathodic compound, the EC composition according to an aspect of the present invention can maintain the transparency.

The effect of steric hindrance in an aspect of the present invention is described taking the anodic EC compound as an example.

FIG. 1 is a view showing Exemplary Compound A-6 which is an example of an organic compound according to an aspect of the present invention in the molecular model. The chemical structural formula of A-6 is shown below.

[Chem. 11]

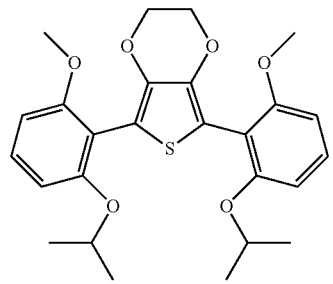

FIG. 1 shows the three-dimensional structure of molecules when A1 to A4 are isopropoxy groups or methoxy groups and X is 3,4-ethylene dioxythiophene among organic compounds according to an aspect of the present invention. The three-dimensional structure illustrated in FIG. 1 is obtained by performing structure optimization calculation in the ground state using Gaussian 03, Revision D.01 which is an electronic state calculation software. At that time, as a quantum chemical calculation method, a density functional theory was adopted and B3LYP was used for the functional. As the basis function, Gaussian 03 was used, and 6-31G* was used in Revision D.01.

Gaussian 03, Revision D.01,
M. J. Frisch, G. W. Trucks, H. B. Schlegel, G. E. Scuseria, M. A. Robb, J. R. Cheeseman, J. A. Montgomery, Jr., T. Vreven,
K. N. Kudin, J. C. Burant, J. M. Millam, S. S. Iyengar, J. Tomasi,
V. Barone, B. Mennucci, M. Cossi, G. Scalmani, N. Rega, G. A. Petersson, H. Nakatsuji, M. Hada, M. Ehara, K. Toyota, R. Fukuda, J. Hasegawa, M. Ishida, T. Nakajima, Y. Honda, O. Kitao,
H. Nakai, M. Klene, X. Li, J. E. Knox, H. P. Hratchian, J. B. Cross,
V. Bakken, C. Adamo, J. Jaramillo, R. Gomperts, R. E. Stratmann,
O. Yazyev, A. J. Austin, R. Cammi, C. Pomelli, J. W. Ochterski,
P. Y. Ayala, K. Morokuma, G. A. Voth, P. Salvador, J. J. Dannenberg,
V. G. Zakrzewski, S. Dapprich, A. D. Daniels, M. C. Strain,
O. Farkas, D. K. Malick, A. D. Rabuck, K. Raghavachari,
J. B. Foresman, J. V. Ortiz, Q. Cui, A. G. Baboul, S. Clifford,
J. Cioslowski, B. B. Stefanov, G. Liu, A. Liashenko, P. Piskorz,
I. Komaromi, R. L. Martin, D. J. Fox, T. Keith, M. A. Al-Laham,
C. Y. Peng, A. Nanayakkara, M. Challacombe, P. M. W. Gill,
B. Johnson, W. Chen, M. W. Wong, C. Gonzalez, and J. A. Pople,
Gaussian, Inc., Wallingford Conn., 2004.

In FIG. 1, 21 denotes a 3,4-ethylene dioxythiophene plane and 22 denotes a phenyl group having an isopropoxy group and a methoxy group. The 3,4-ethylene dioxythiophene plane which is a part showing the EC property is structured so that the part is difficult to achieve intermolecular contact with other molecules by the phenyl group having A1 to A4 which are the terminal parts of the molecules.

Consequently, since an enclosed molecular shape is formed, the contact with the cathodic EC compound is suppressed. Bulky steric hindrance groups represented by A1 to A4 suitably have an excluded volume equal to or larger than that of a methyl group.

The excluded volume can be determined by molecular orbital calculation or the like.

The cathodic EC compound becomes a steric hindrance group by giving a benzyl group to the 4,4'-bipyridinium salt (viologen) part which is the EC part, so that the contact with the anodic EC compound is suppressed, and thus the electronic CT interaction decreases. Although the effect of steric hindrance is demonstrated by only a benzyl group, it is more suitable that the substituents represented by R20 and R21 in General Formula [2] are substituted with a benzyl group.

The transparency of a composition has decreased only by giving a steric hindrance group to only either the anodic EC compound or the cathodic EC compound. Therefore, it is suitable for both the anodic EC compound and the cathodic EC compound to have a steric hindrance substituent. Due to the fact that both the anodic EC compound and the cathodic EC compound have a substituent which is a steric hindrance group, the effect of reducing the CT interaction is demonstrated.

The EC composition according to an aspect of the present invention has an electrochromic compound represented by General Formula [1] and an electrochromic compound represented by General Formula [2]. The weight ratio of the electrochromic compound represented by General Formula [1] contained in the EC composition is suitably 10% by mol or more and 90% by mol or less and suitably 40% by mol or more and 60% by mol or less when the total of the electrochromic compound represented by General Formula [1] and the electrochromic compound represented by General Formula [2] is 100% by mol.

Specific structural formulae of the anodic EC compound represented by General Formula [1] and the cathodic EC compound represented by General Formula [2] according to an aspect of the present invention are shown below. However, the EC compounds of the present invention are not limited thereto.

[Chem. 12]

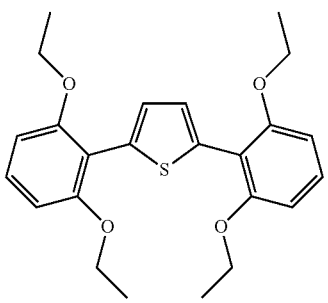

A-1

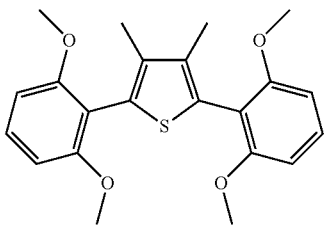

A-2

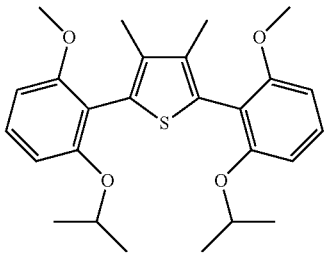

A-3

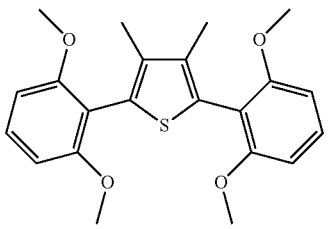

A-4

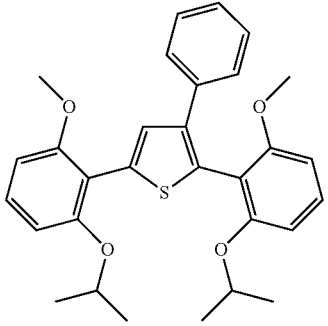

A-5

[Chem. 13]
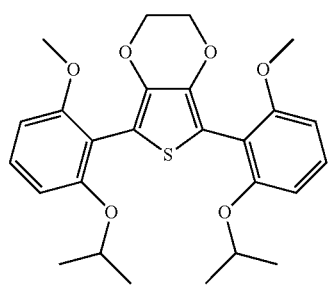 A-6
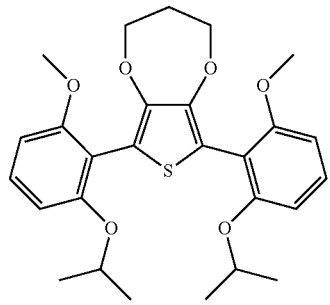 A-7
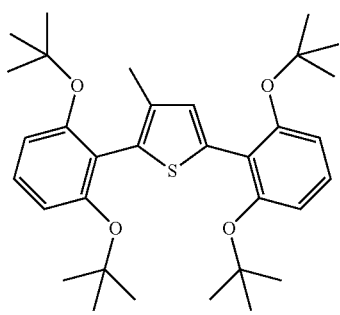 A-8
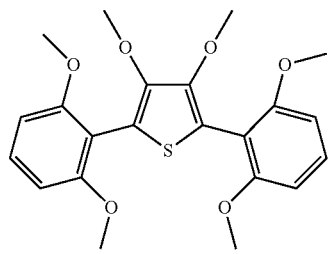 A-9
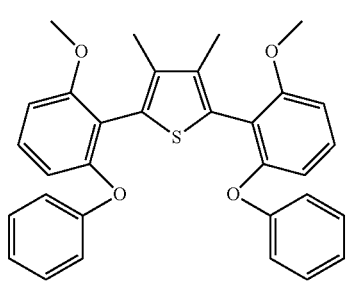 A-10
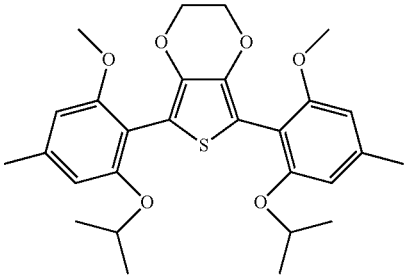 A-11
[Chem. 14]
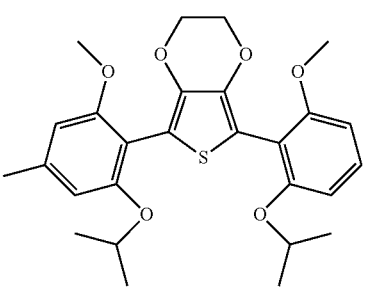 A-12
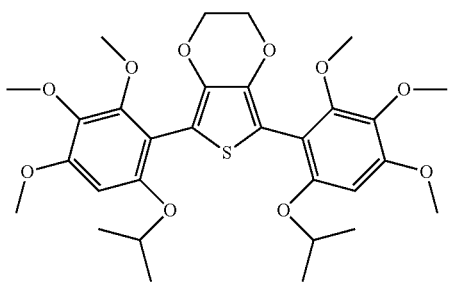 A-13
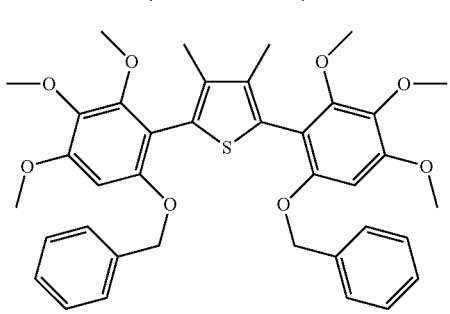 A-14
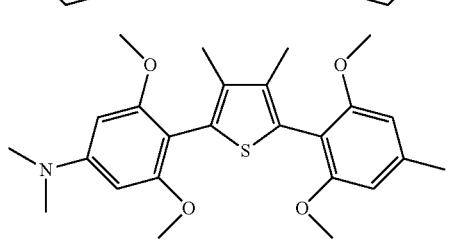 A-15
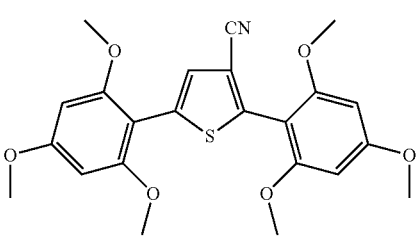 A-16

A-17
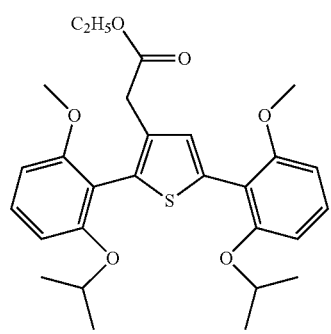
A-18
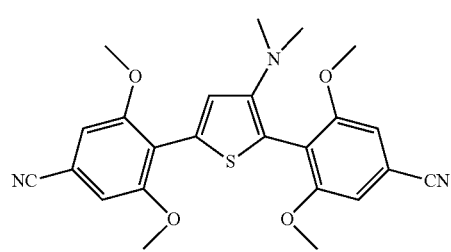
[Chem. 15]
A-19
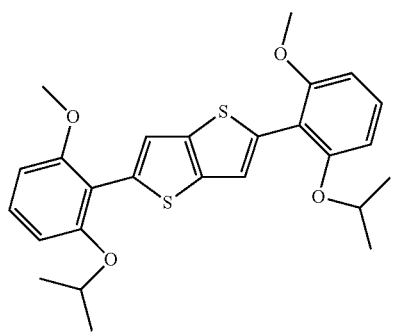
A-20
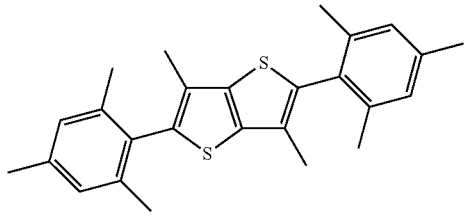
A-21
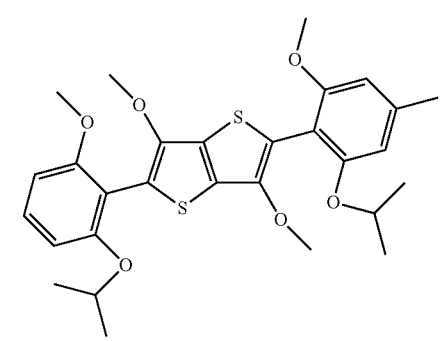
A-22
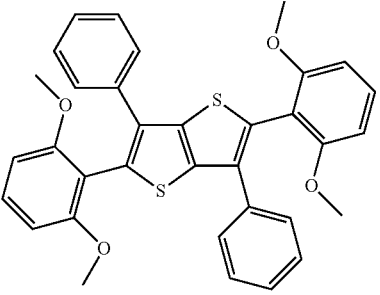
A-23
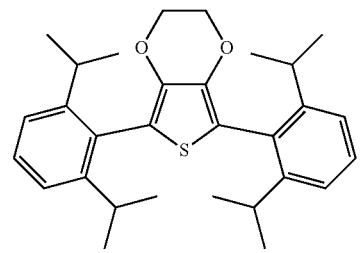
A-24
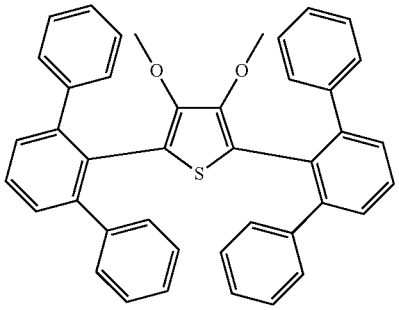
[Chem. 16]
A-25
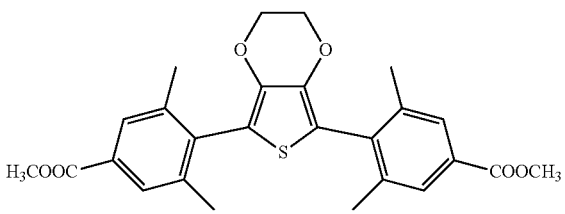
A-26
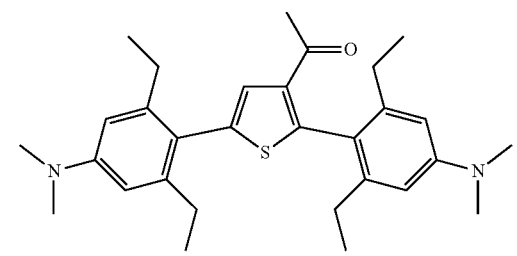

[Chem. 17]
A-27
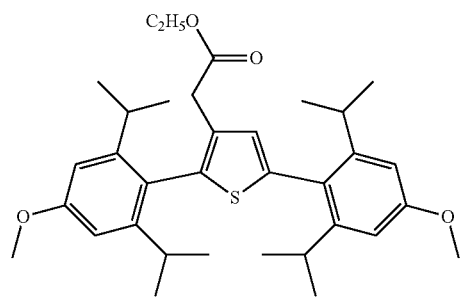
A-28
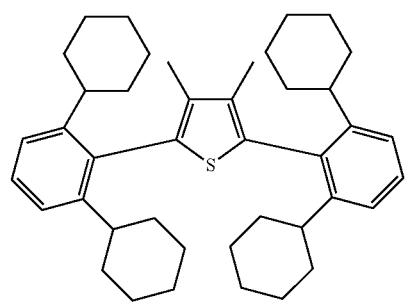
A-29
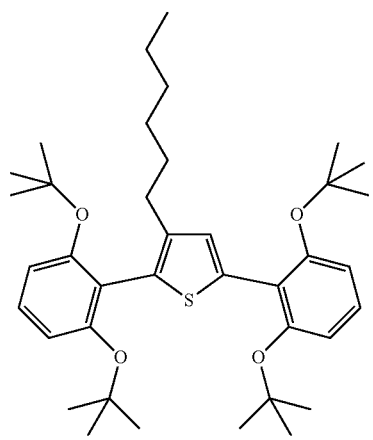
A-30
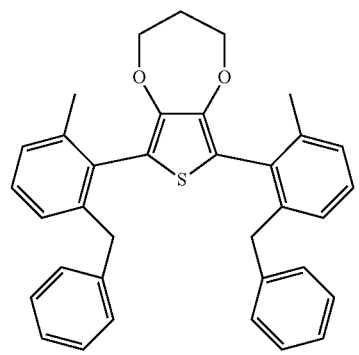
A-31
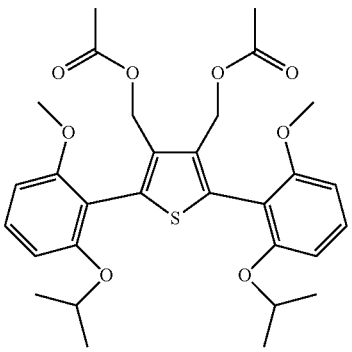
A-32
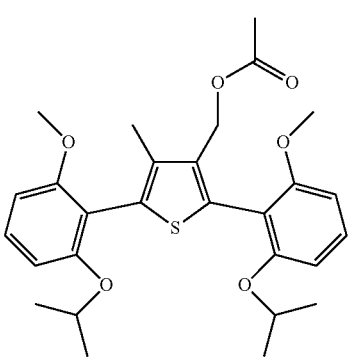
[Chem. 18]
B-1
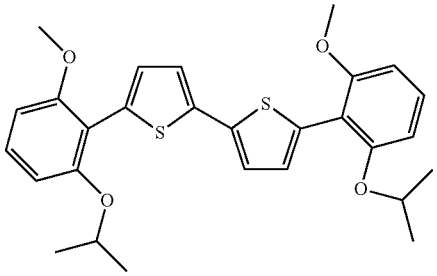
B-2
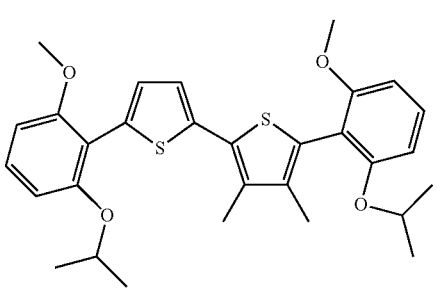
B-3
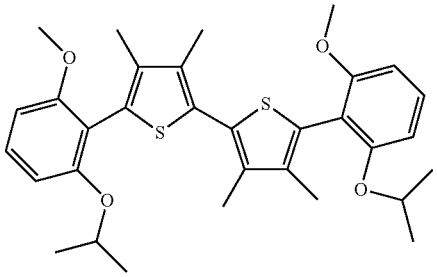

-continued
B-4
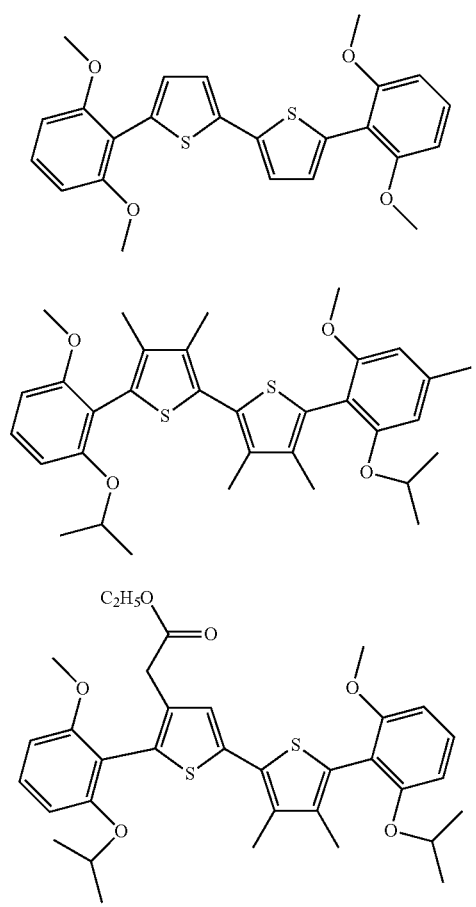
B-5
B-6
[Chem. 19]
B-7
B-8
-continued
B-9
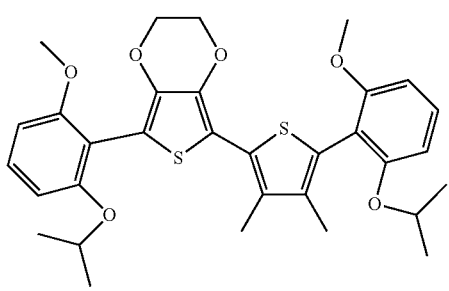
B-10
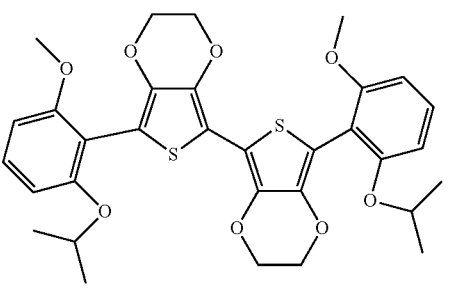
B-11
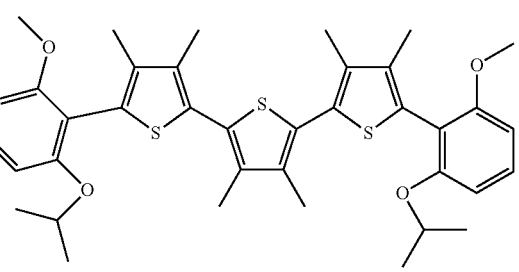
[Chem. 20]
B-12
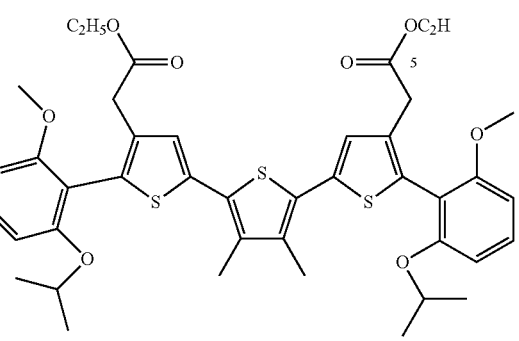
B-13
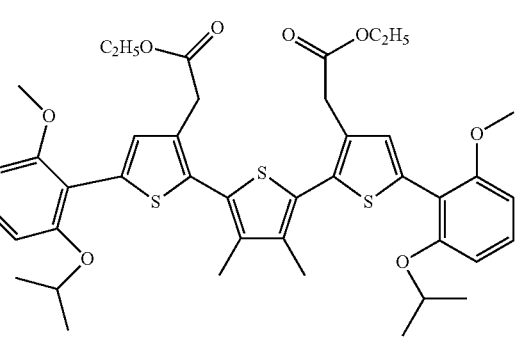

-continued
B-14
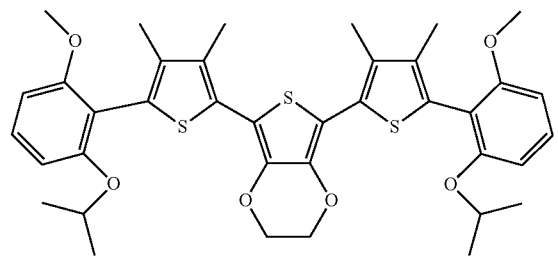
B-15
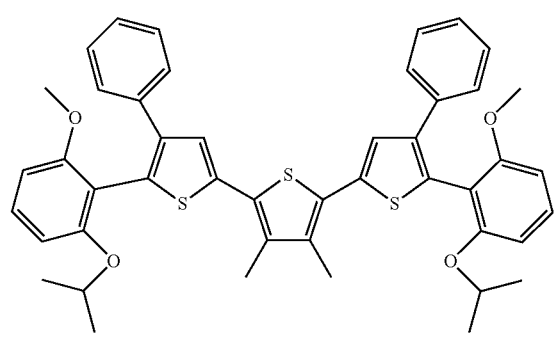
B-16
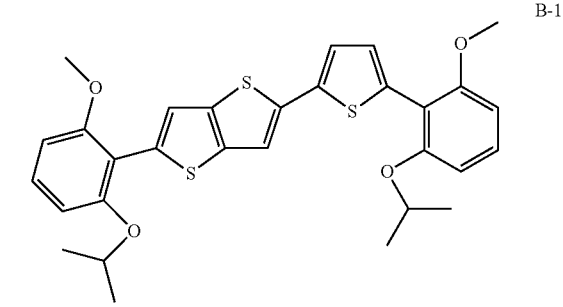
B-17
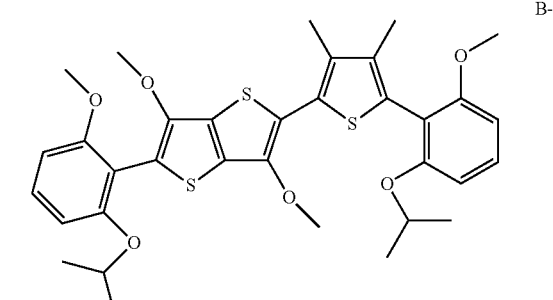
B-18
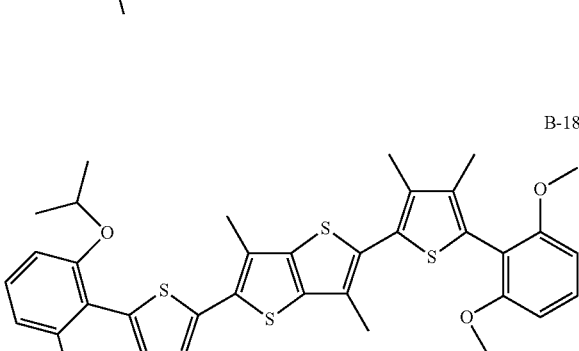
[Chem. 21]
B-19
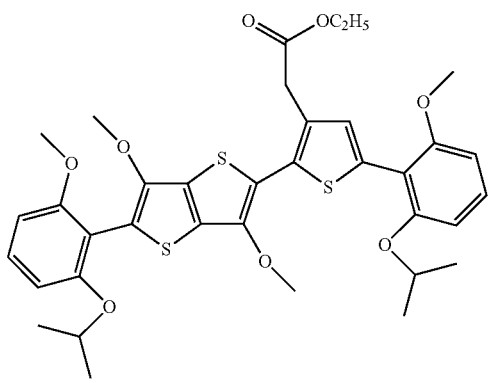
B-20
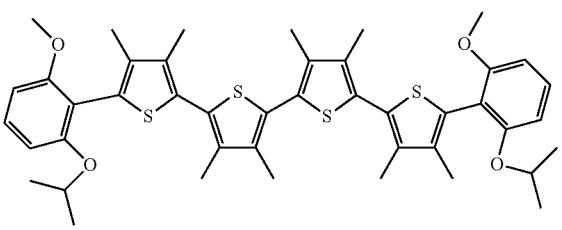
B-21
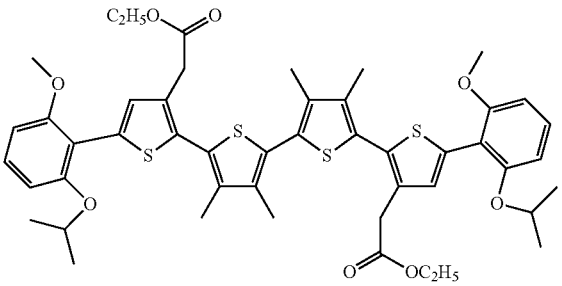
B-22
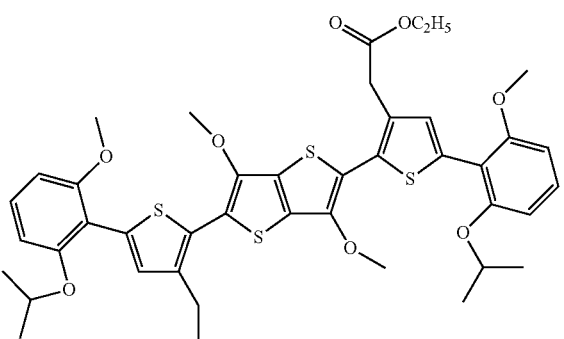
B-23
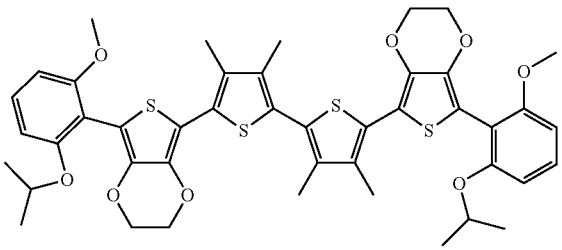

B-24
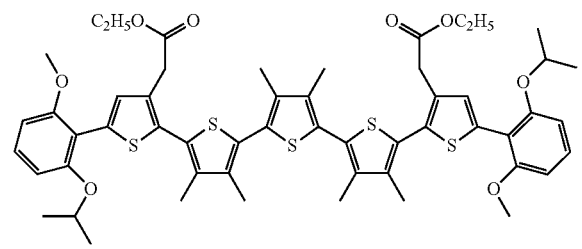
[Chem. 22]
B-25
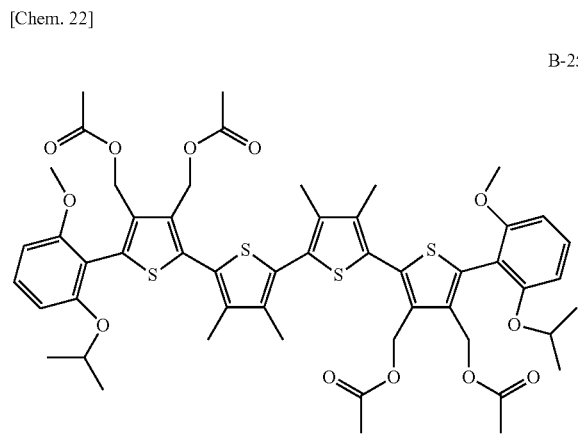
B-26
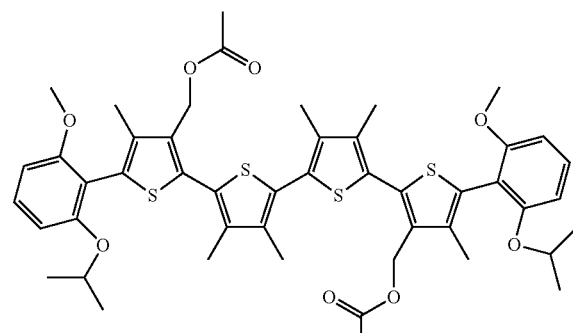
B-27
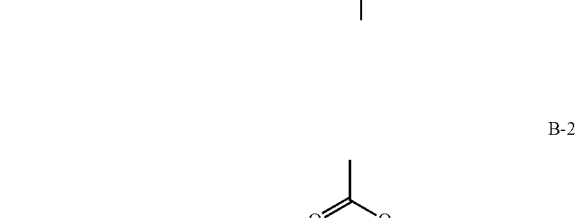
B-28
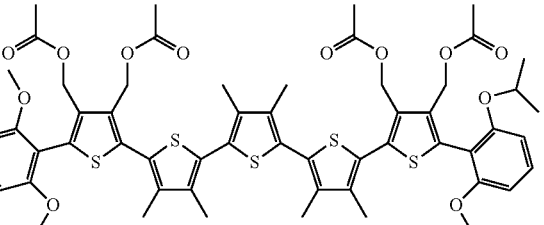
[Chem. 23]
C-1
C-2
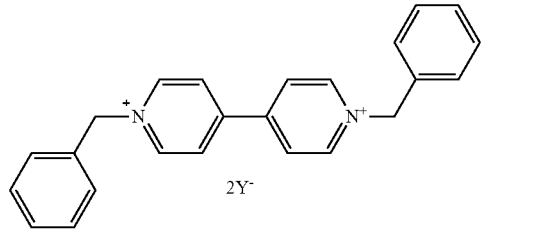
C-3
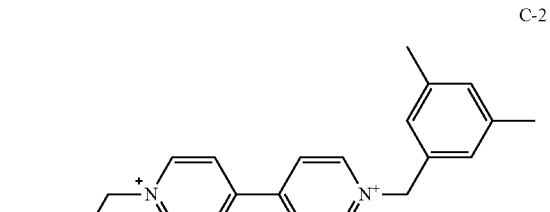
C-4
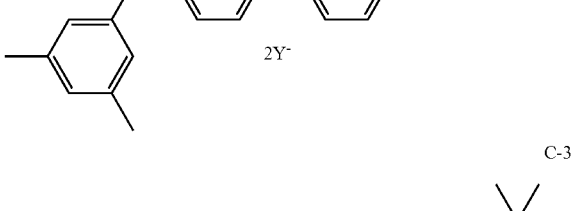

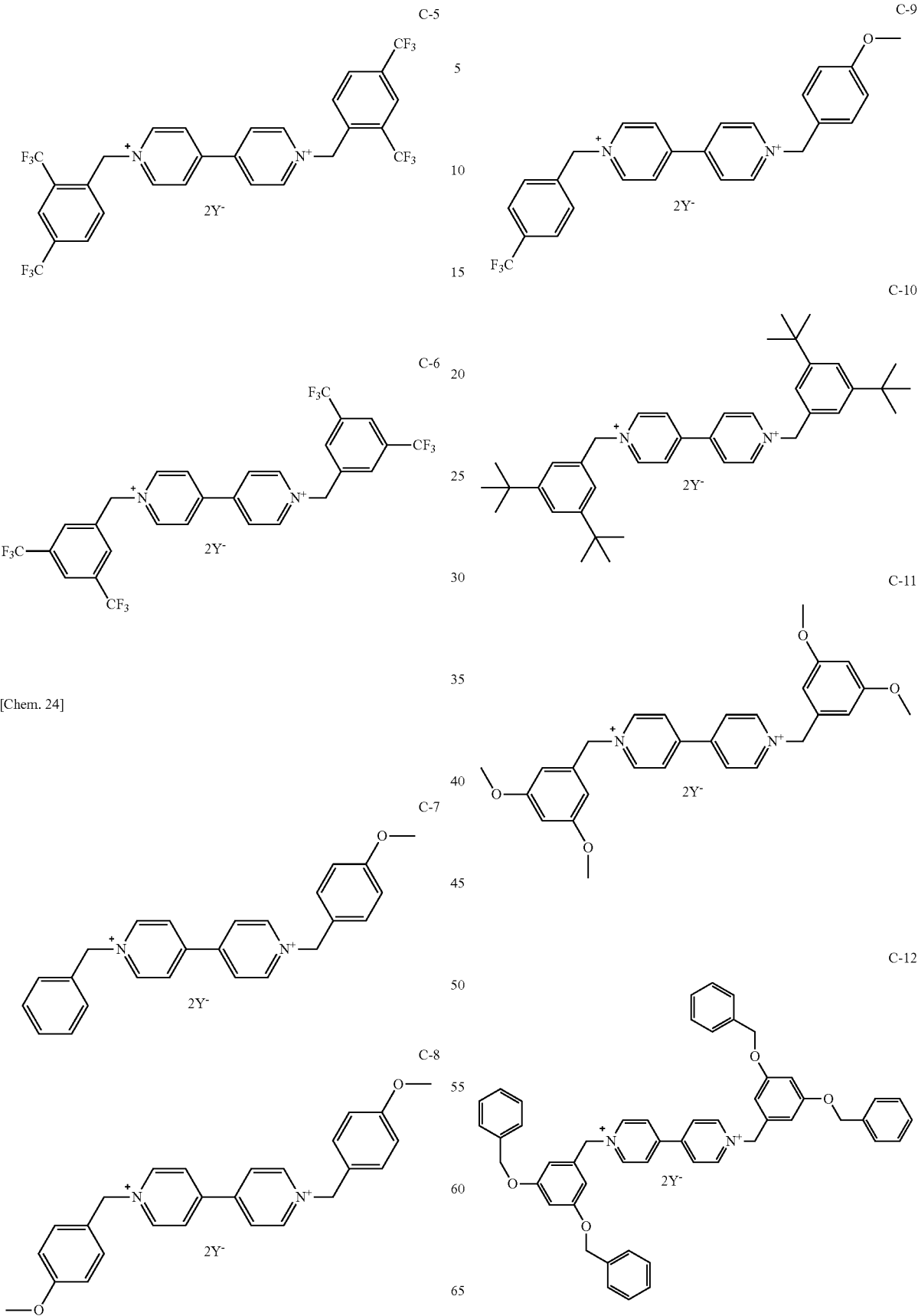

[Chem. 25]
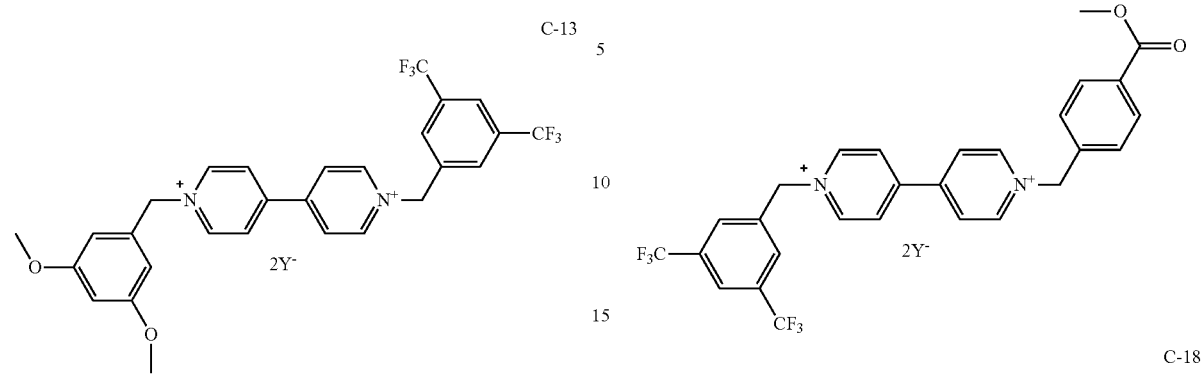
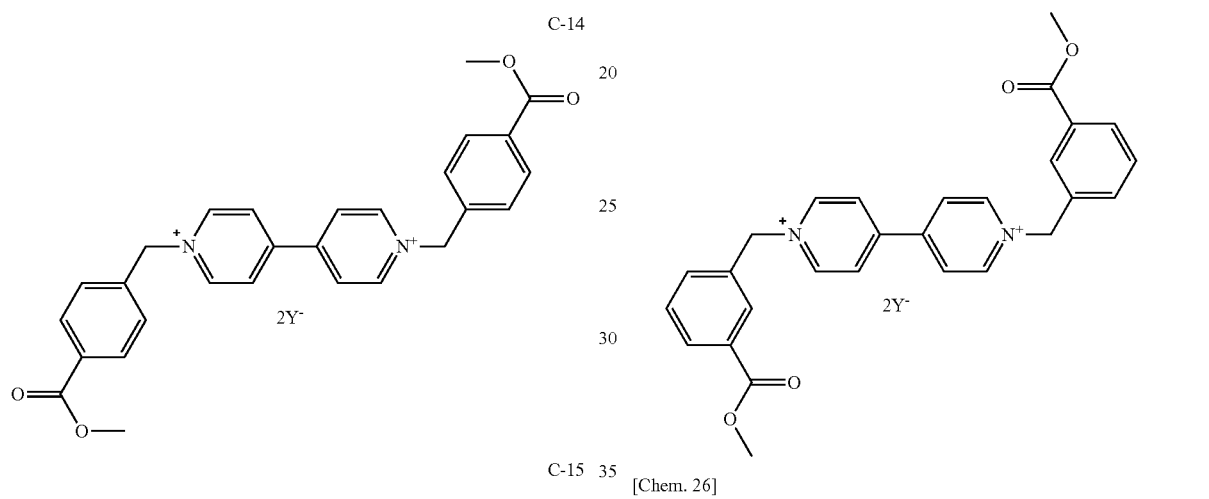
[Chem. 26]
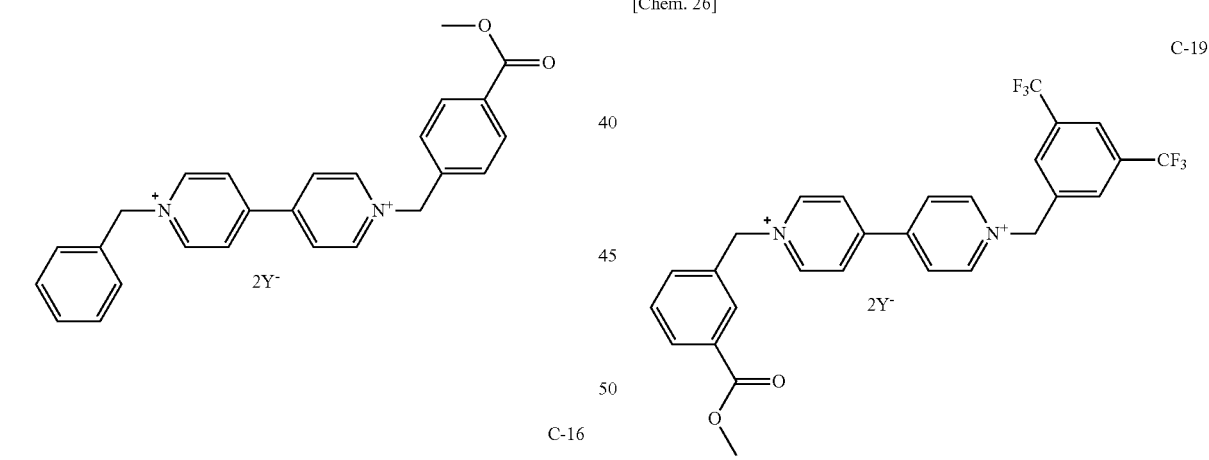
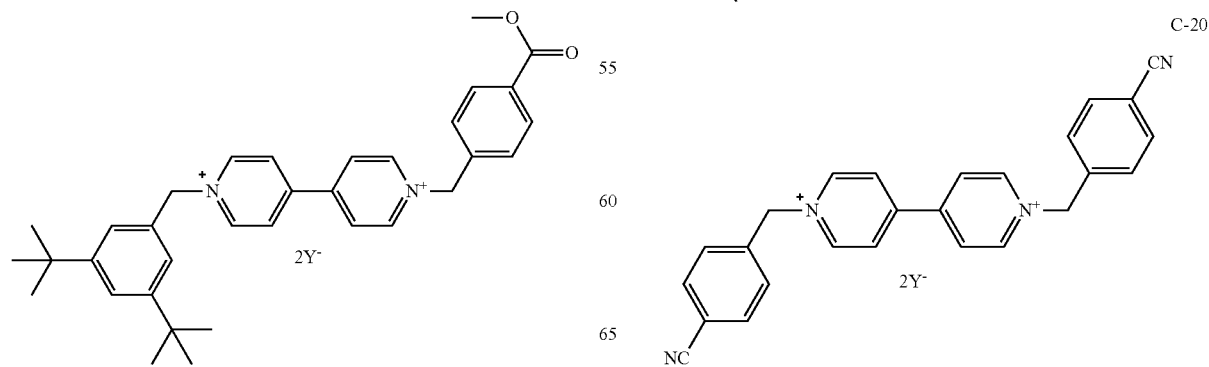

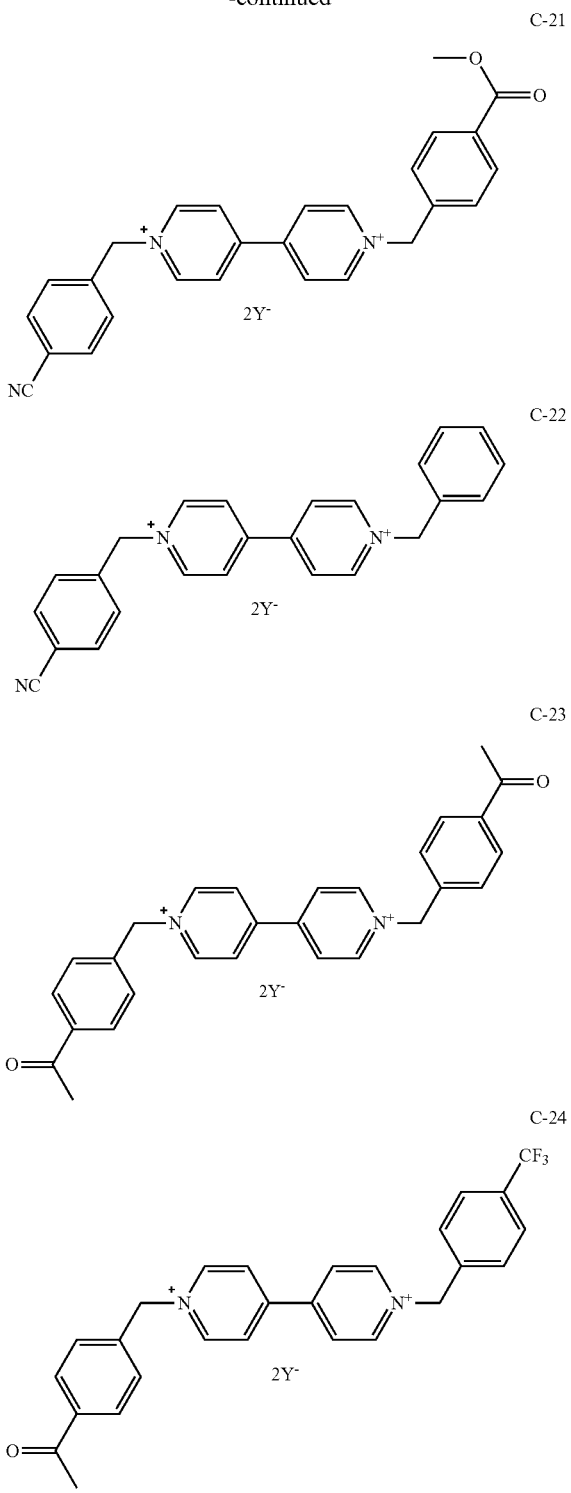

Among the exemplary compounds, the compounds shown in A group and B group are examples of the anodic EC compound represented by General Formula [1] and the compounds shown in C group are examples of the cathodic EC compound represented by General Formula [2].

The compounds shown in A group are compounds in which n in General Formula [1] is 1. More specifically, the repeating unit of the thiophene compound is 1. The compounds shown in B group are compounds in which the substituents represented by A1 to A4 contained in the phenyl group at the terminal part are a methoxy group and an isopropoxy group and n is 2 to 5 in General Formula [1].

On the other hand, the compounds shown in C group are examples of compounds in which the substituents represented by R20 and R21 in General Formula [2] have various structures at a viologen part.

In all the anodic EC compounds of A group and B group, the substituents represented by A1 to A4 are introduced into the phenyl group at the terminal part. A benzyl group which may have a substituent is introduced into all the cathodic EC compounds of C group. Therefore, both the EC parts of the thiophene part and the viologen part which show the EC property are structured to be hard to approach each other due to the steric hindrance of the substituents. As a result, the CT interaction is suppressed, and an effect of maintaining high transparency is demonstrated.

Other Components Configuring Electrochromic Composition

The EC composition according to an aspect of the present invention may have, in addition to the electrochromic compound represented by General Formula [1] and the electrochromic compound represented by General Formula [2], a third EC compound of another type, which is different from both the electrochromic compounds represented by General Formula [1] and General Formula [2], as the EC compound contained in the electrochromic composition. By using light absorption by the third EC compound in addition to the light absorption in a visible light region in coloring by the EC compound of General Formula [1] and the EC compound of General Formula [2] according to an aspect of the present invention, the transmittance in the entire visible light region can be set to a transmittance equal to or less than a certain transmittance in coloring.

Specific examples of the third EC compound described above include anodic EC compounds, such as a ferrocene derivative, a phenylene diamine derivative, a triphenyl amine derivative, and a phenazine derivative, and cathodic EC compounds, such as an anthraquinone derivative and a ferrocenium salt derivative.

The EC composition according to an aspect of the present invention may contain a solvent which dissolves the anodic EC compound and the cathodic EC compound. As a specific example, the solvent is not particularly limited insofar as the EC compound can be dissolved but solvents having polarity are particularly suitable.

Specific examples include water and organic polar solvents, such as methanol, ethanol, propylene carbonate, ethylene carbonate, dimethylsulfoxide, dimethoxy ethane. γ-butyro lactone, γ-valero lactone, sulfolane, dimethyl formamide, dimethoxy ethane, tetrahydrofuran, acetonitrile, propione nitrile, 3-methoxy propionitrile, benzonitrile, dimethyl acetamide, methylmethylpyrrolidone, and dioxolane.

Furthermore, those whose viscosity is increased or formed into a gel by blending a polymer or a gelling agent in the EC medium mentioned above and the like can also be used.

The polymer is not particularly limited and examples of the polymer include polyacrylonitrile, carboxymethylcellulose, polyvinyl chloride, polyethylene oxide, polypropylene oxide, polyurethane, polyacrylate, polymethacrylate, polyamide, polyacrylamide, polyester, Nafion (Registered Trademark), and the like, for example.

Any substance is used as an electrolyte without limitation insofar as the substance is an ion dissociative salt and shows good solubility in solvents and high compatibility in solid electrolytes. In particular, substances having an electron donating property are suitable.

Moreover, an electrolyte may be added to the EC composition according to an aspect of the present invention. Examples of the electrolyte include various kinds of alkaline metal salts, inorganic ion salts, such as alkaline earth metal salts, quaternary ammonium salts, cyclic quaternary ammonium salts, and the like, for example. These electrolytes are also referred to as supporting electrolytes.

Specific examples include alkaline metal salts of Li, Na, and K, such as $LiClO_4$, $LiSCN$, $LiBF_4$, $LiAsF_6$, $LiCF_3SO_3$, $LiPF_6$, $LiI$, $NaI$, $NaSCN$, $NaClO_4$, $NaBF_4$, $NaAsF_6$, $KSCN$, and $KCl$, and quaternary ammonium salts and cyclic quaternary ammonium salts, such as $(CH_3)_4NBF_4$, $(C_2H_5)_4NBF_4$, $(n-C_4H_9)_4NBF_4$, $(C_2H_5)_4NBr$, $(C_2H_5)_4NClO_4$, and $(n-C_4H_9)_4NClO_4$, and the like.

The EC composition according to an aspect of the present invention may be an EC composition having a solvent, the electrochromic compound represented by General Formula [1], the electrochromic compound represented by General Formula [2], and an electrolyte. The concentration of the electrolyte is suitably larger than 0 mol/l and 10 mol/l or less in a solvent. The concentration is suitably larger than 0.1 mol/l and 5.0 mol/l or less and more suitably larger than 0.1 mol/l and 1.0 mol/or less.

Method for Synthesizing EC Compound

The compound represented by General Formula [1] according to an aspect of the present invention can be synthesized by a coupling reaction using a known Pd catalyst. The anodic EC compound according to this embodiment can be synthesized by a coupling reaction using a Pd catalyst in a combination of a halogenated thiophene compound which shows the EC property and boronic acid or boronic acid ester of a compound forming a terminal unit or in a combination of boronic acid or boronic acid ester of a thiophene compound which shows the EC property and a halogenated compound forming a terminal unit. Specifically, the anodic EC compound according to this embodiment can be synthesized as follows. Herein, a compound in which the core part is thiophene is shown as an example. By changing the core part as appropriate, the compound represented by General Formula [1] can be synthesized.

[Chem. 27]

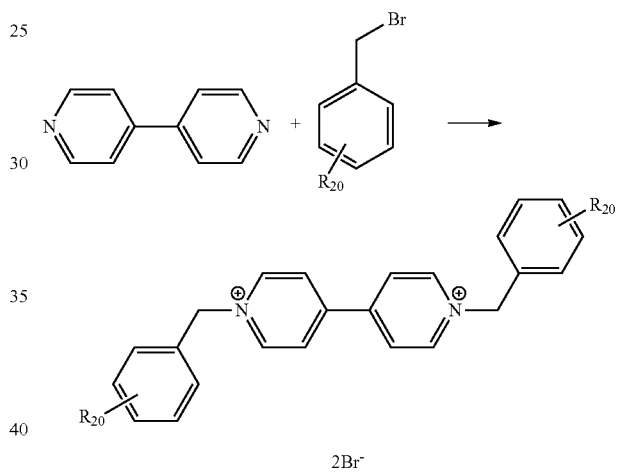

The cathodic EC compound [2] according to an aspect of the present invention can be synthesized by the following synthesis example. R20s in the synthesis example may be substituents different from each other. When two R20s are substituents different from each other, one of them is indicated as R21. By changing R20 as appropriate, the compound represented by General Formula [2] can be synthesized. Specifically, the compound represented by General Formula [2] can be synthesized by a reaction of 4,4'-bipyridine and benzyl bromide which may have a substituent.

[Chem. 28]

An electrochromic element according to an aspect of the present invention has a pair of electrodes configured from a first electrode and a second electrode and an electrochromic composition disposed between the pair of electrodes, in which the electrochromic composition has at least one kind of each of the anodic electrochromic compound represented by General Formula [1] and the cathodic electrochromic compound represented by General Formula [2].

Figure 2:
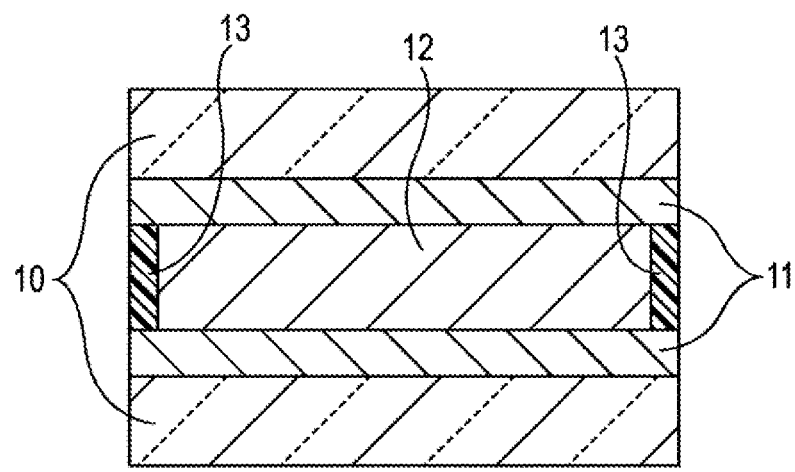
FIG. 2 is a schematic cross-sectional view showing an example of an embodiment of an EC element according to an aspect of the present invention.
Figure 1B:
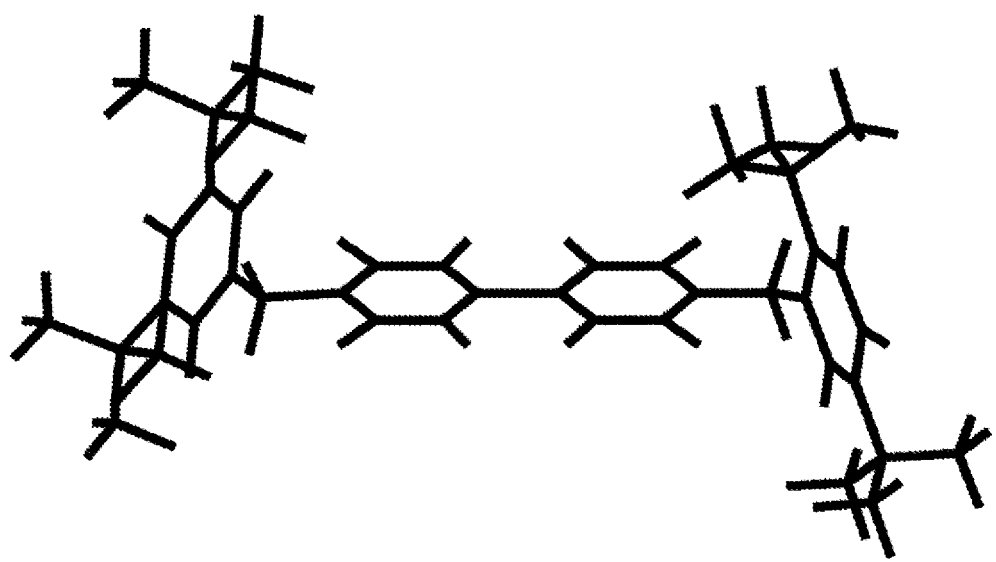
FIG. 1B is a view showing an example of a cathodic EC compound configuring an EC composition according to an aspect of the present invention in the molecular model.
Figure 1C:
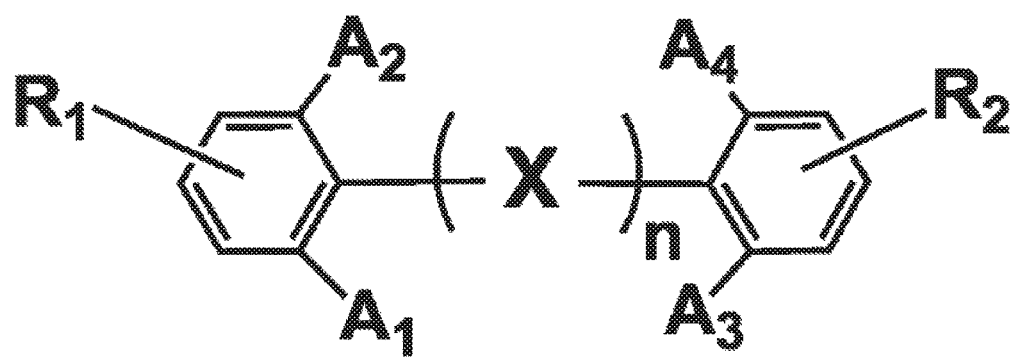
FIG. 1C shows an anodic electrochromic compound represented by General Formula [1] and a cathodic electrochromic compound represented by General Formula [2].
Figure 1C:
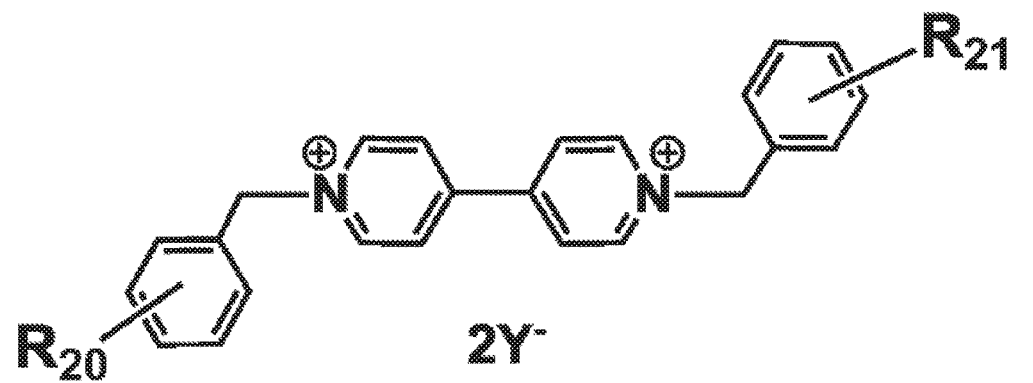

Hereinafter, the electrochromic element (EC element) according to an aspect of the present invention is described with reference to the drawings. FIG. 2 is a schematic cross-sectional view showing an example of an embodiment of the EC element according to an aspect of the present invention.

The EC element of FIG. 2 contains a pair of transparent electrodes 11 configured from a first electrode and a second electrode and an EC composition 12 containing at least one kind of each of the anodic EC compound represented by General Formula [1] and the cathodic EC compound represented by General Formula [2] disposed between the pair of electrodes. The electrode distance between the pair of electrodes is made constant by spacers 13.

In the EC element, a pair of electrodes is disposed between a pair of transparent substrates 10.

Herein, the transparency means that the light transmittance in a visible light region is 40% or more and 100% or less. However, the EC element described above is an example of the EC element configuration according to an aspect of the present invention and the EC element according to an aspect of the present invention is not limited thereto.

For example, a layer of an antireflection film may be provided between the transparent substrate 10 and the transparent electrode 11 or between the transparent electrode 11 and the organic EC composition medium 12. Between the pair of electrodes, a solvent and an electrolyte may be contained in addition to the electrochromic compound.

Next, the transparent substrate and the transparent electrode are described. As the transparent substrate 10, colorlessness or colored glass, tempered glass, and the like are used, and also colorless or colored transparent resin is used, for example.

Specific examples include polyethylene terephthalate, polyethylene naphthalate, polynorbornene, polyamide, polysulfone, polyether sulfone, polyetheretherketone, polyphenylene sulfide, polycarbonate, polyimide, polymethyl methacrylate, and the like.

Examples of materials of the transparent electrode 11 include metals and metal oxides, such as indium tin oxide alloy (ITO), fluorine doped tin oxide (FTO), tin oxide (NESA), indium oxide zinc (IZO), silver oxide, vanadium oxide, molybdenum oxide, gold, silver, platinum, copper, indium, and chromium, silicon materials, such as polycrystalline silicon and amorphous silicon, carbon materials, such as carbon black, graphite, and glassy carbon, and the like, for example.

Moreover, conductive polymers whose conductivity is increased by doping treatment or the like (for example, complexes of polyaniline, polypyrrole, polythiophene, polyacetylene, polyparaphenylene, and polyethylene dioxythiophene (PEDOT) and polystyrene sulfonate, and the like) are also suitably used.

In an optical filter according to this embodiment is required to also have transparency as an optical filter. Therefore, ITO, FTO, IZO NESA, conductive polymers, whose conductivity is increased, which do not exhibit light absorption in a visible light region are suitably used. As a method for increasing the conductivity, known methods can be used.

These substances can be used in various forms, such as a form of a bulk and a form of fine particle. These electrode materials may be used alone or two or more kinds thereof in combination.

The spacers 13 are disposed between the pair of electrodes 11 and give a space for containing the EC composition 12. Specifically, polyimide, Teflon (Registered Trademark), fluororubber, epoxy resin, and the like can be used. By the spacers, the distance between the electrodes of the EC element can be maintained.

The EC element according to this embodiment may have a liquid injection port formed by the pair of electrodes and the spacers. An EC composition is charged from the injection port. Then, the injection port is covered with a sealing member, and then hermetically sealed with an adhesive or the like.

The sealing member also has a role of isolating the adhesive and the EC compound in such a manner that the adhesive and the EC compound do not contact. The shape of the sealing member is not particularly limited and is suitably a tapered shape, such as a wedge shape.

A method for forming the EC element according to this embodiment is not particularly limited and a method including injecting liquid 12 of an EC composition prepared beforehand into a gap formed between the pair of electrode substrates by a vacuum injection method, an air injection method, a meniscus method, or the like.

The EC element according to an aspect of the present invention can be used as a constituent member of an optical filter, a lens unit, an imaging device, and a window material.

Figure 6A:
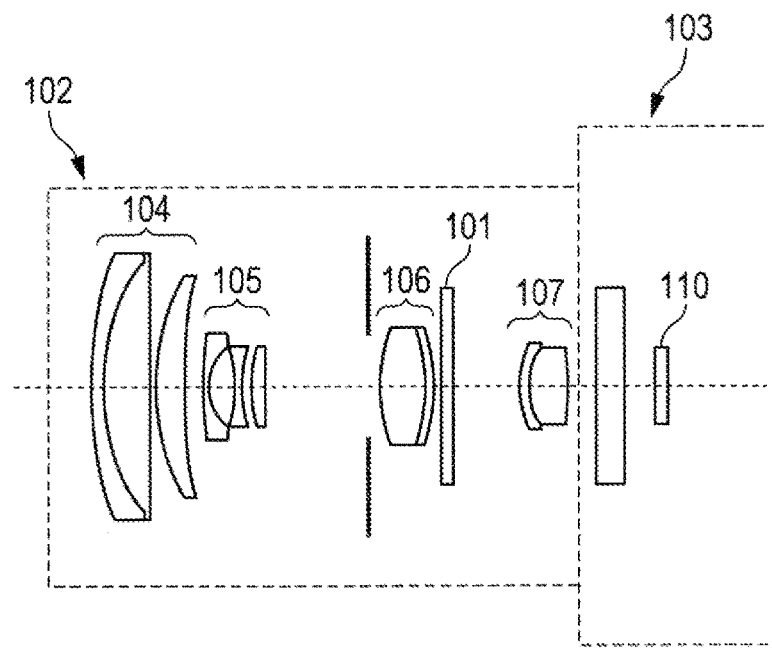
FIG. 6A is a view showing an example of an image pick up apparatus according to an aspect of the present invention.
Figure 6B:
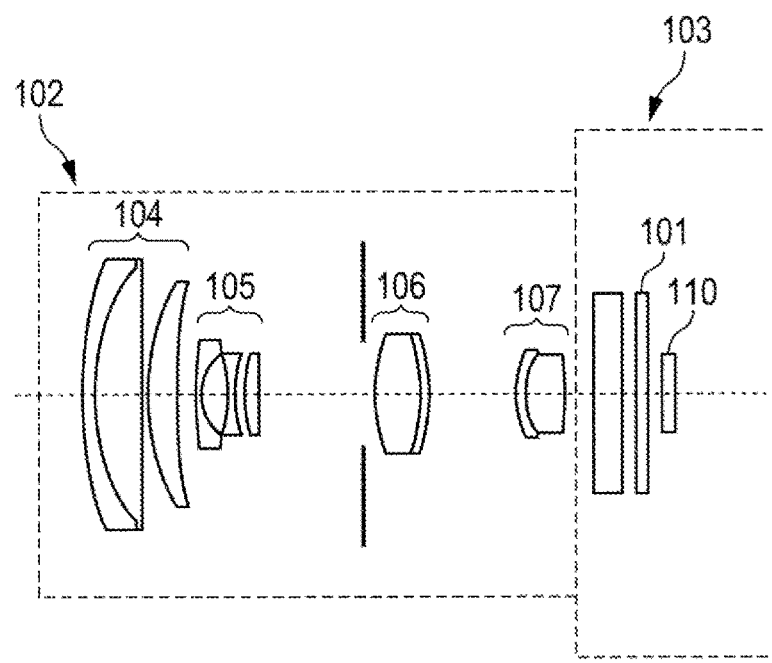
FIG. 6B is a view showing an example of a lens unit according to an aspect of the present invention.

The EC element according to this embodiment has sufficiently high transparency in decoloration and also shows a high absorptivity in a specific visible light wavelength band or, by mixing a plurality of EC compounds, over the entire visible light region in coloring. Therefore, the EC element according to this embodiment can be suitably used for controlling the amount of incident light into an image pickup device 103 (FIGS. 6A, 6B), such as a camera, and controlling the incident wavelength distribution characteristic.

The control of the incident wavelength distribution is effective for color temperature conversion in imaging. The EC element covering the entire visible light region in coloring can be suitably used as an ND filter. In this case, when blending the third EC compound other than the compounds represented by General Formulae [1] and [2] according to an aspect of the present invention in the EC layer 12, it is suitable to select a compound as appropriate in such a manner as to obtain an EC element which uniformly absorbs light in a visible light region at each wavelength.

More specifically, by providing the EC element in an optical path of an imaging optical system connected to an image pickup device, the light quantity received by an image pickup device or the incident wavelength distribution characteristic can be controlled. The imaging optical system can also be referred to as a lens system. As the imaging optical system, a lens unit 102 having a plurality of lenses 104, 105, 106, 107 (FIGS. 6A and 6B) and the like are mentioned.

The optical filter according to an aspect of the present invention has the EC element according to an aspect of the present invention and an active element electrically connected to the EC element. Specific examples of the active element electrically connected to the EC element include a switching element for controlling the transmittance of the EC element. Examples of the switching element include TFT and MIM elements, for example. The TFT is also referred to as a thin film transistor and a semiconductor and an oxide semiconductor are used as constituent materials thereof. Specifically, a semiconductor containing amorphous silicon, low-temperature polysilicon, and InGaZnO as constituent materials and the like are mentioned.

The lens unit 102 according to an aspect of the present invention has a plurality of lenses and an optical filter having the EC element. The optical filter configuring the lens unit may be provided between the plurality of lenses or may be provided outside the lens. The optical filter is suitably provided on the optical axis of the lens.

The imaging device 103 according to an aspect of the present invention has an optical filter and a light receiving element for receiving light passing through the optical filter 101.

Specific examples of the imaging device include a camera, a video camera, a cellular phone with camera, and the like. The imaging device may have an aspect in which a body having a light receiving element 110 (FIGS. 6A and 6B) and a lens unit having a lens can be separated. Herein, when the body and the lens unit can be separated in the imaging device, the imaging device may have an aspect in which an optical filter separately provided from the imaging device may be used in imaging. In such a case, as the arrangement position of the optical filter, the optical filter is provided outside the lens unit, between the lens unit and the light receiving element, between the plurality of lenses, or the like.

Figure 7A:
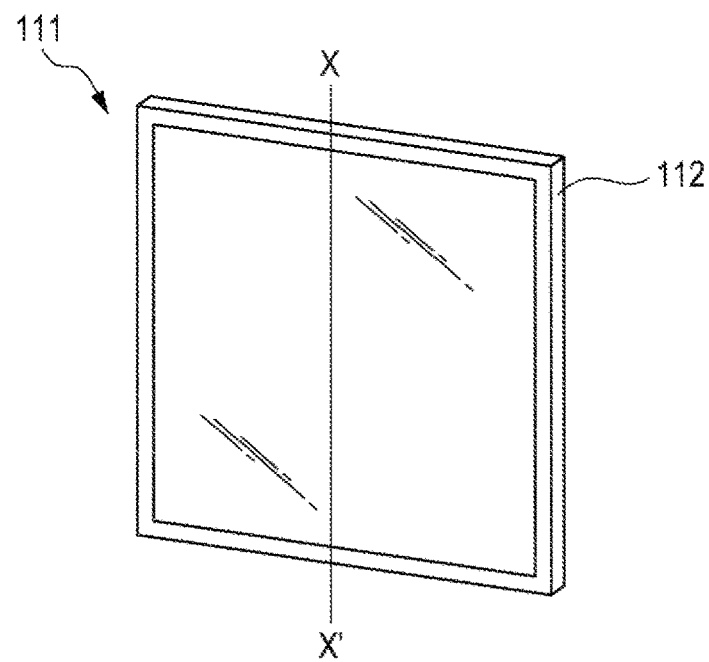
FIG. 7A is a view showing an example of a light control window according to an aspect of the present invention.
Figure 7B:
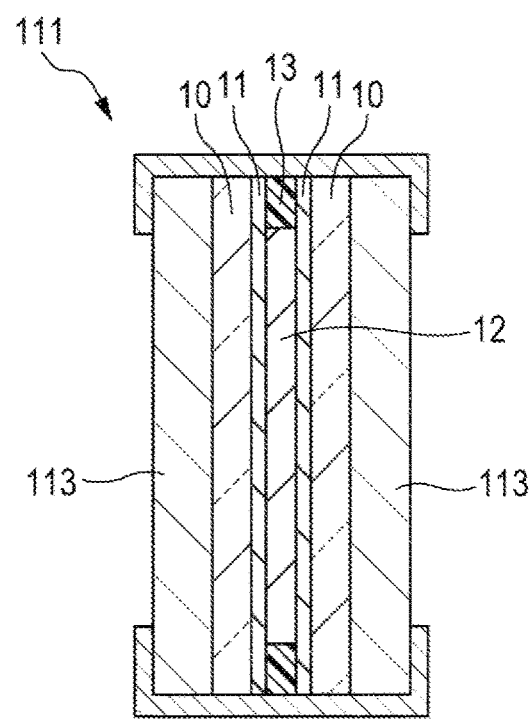
FIG. 7B is a cross-sectional view taken of the example light control window of FIG. 7A taken along line X-X' of FIG. 7A.

The window material 111, 112 (FIGS. 7A and 7B) according to an aspect of the present invention has a pair of transparent substrates 113 (FIGS. 7A and 7B), an EC element provided between the transparent substrates, and an active element connected to the EC element. The active element controls the transmittance of the EC element. The active element may be a switching element or an amplification element. Specifically, a transistor is mentioned. The transistor may have an oxide semiconductor in an active region thereof. Although the active element is connected to the EC element, the connection manner to the EC element may be direct connection or indirect connected through another element. The window material according to an aspect of the present invention can be used for windows of airplanes, cars, residences, and the like. The window material having the EC element can also be referred to as a window material having an electronic curtain.

Since the EC element can demonstrate high transparency in a decolored state, sufficient transmitted light quantity to incident light can be obtained and, in a colored state, an optical property in which incident light is certainly blocked and modulated can be obtained.

EXAMPLES

The anodic EC compound configuring the EC composition according to this embodiment can be synthesized based on a synthesis method described in the synthesis example. A more specific example of the synthesis method is described below. A desired anodic EC compound can be synthesized by changing as appropriate the structures of a thiophene derivative part which shows the EC property and a phenyl group at a terminal part in the synthesis example.

Synthesis Example 1: Synthesis of Exemplary Compound B-4

[Chem. 29]

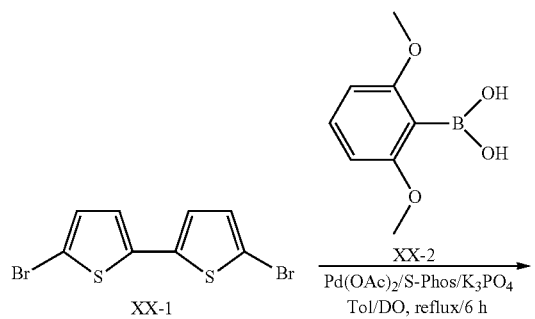

In a 50 mL reaction vessel, 300 mg (0.926 mmol) of XX-1 (5,5'-dibromo-2,2'-bithiophene) and 590 mg (3.24 mmol) of XX-2 were mixed with a toluene/1,4-dioxane (6 ml/6 ml) mixed solvent, and then dissolved oxygen was removed with nitrogen. Subsequently, 8.3 mg (0.037 mmol) of Pd(OAc)$_2$ and 38 mg (0.093 mmol) of 2-dicyclohexyl phosphino-2', 6'-dimethoxy biphenyl (S-Phos), and 1.07 g (4.65 mmol) of tripotassium phosphate were added under a nitrogen atmosphere, heated and refluxed at 100° C., and then reacted for 6 hours. The reaction solution was cooled to room temperature, concentrated under reduced pressure, and then isolated and purified by silica gel chromatography (Mobile phase: Hexane/Chloroform=1/3), whereby B-4 of light yellow solid powder was obtained (240 mg).

As a result of confirming the structure of the compound B-4 by measurement of mass-spectrum (MS) measurement and nuclear magnetic resonance spectrum (NMR) measurement, the molecular weight and the ratio of the NMR peak integrated values were well in agreement with the structure. Specifically, 438 which is M+ of this compound was confirmed by matrix assisted laser desorption ionization mass spectrum (MALDI-MS) measurement. The measurement results of the NMR spectrum are shown below.

$^1$H-NMR (CDCl$_3$) δ (ppm): 7.41 (d, 2H), 7.23 (t, 2H), 7.18 (d, 2H), 6.65 (d, 4H), 3.86 (s, 12H).

Synthesis Example 2: Synthesis of Exemplary Compound A-14

[Chem. 30]

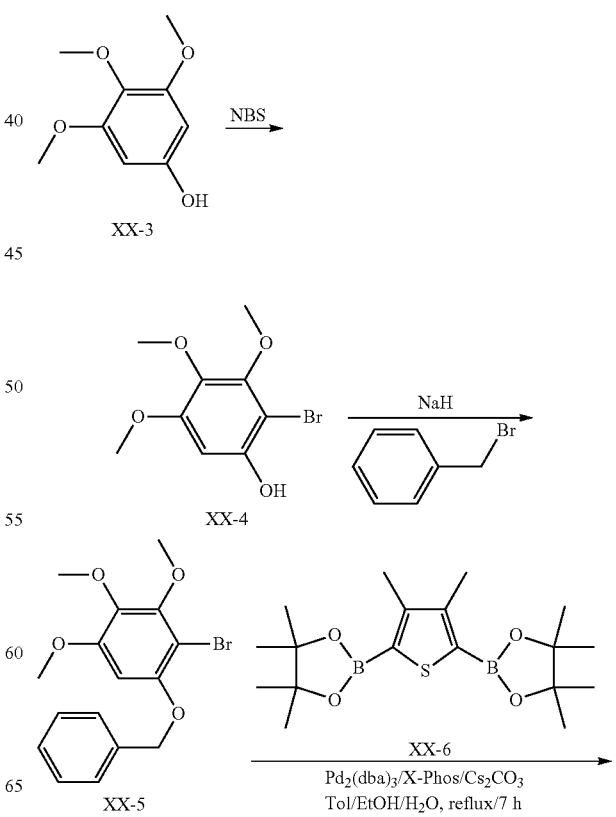

-continued

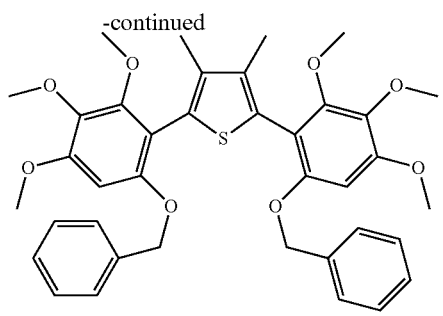

A-14

(1) In a 100 mL reaction vessel, 2.0 g (10.8 mmol) of XX-3 was dissolved in 20 ml of THF. Subsequently, 1.93 g (10.8 mmol) of N-bromosuccinimide was added, and then stirred at room temperature for 2 hours. Water was added to the reaction solution, and then a precipitate was extracted with ethyl acetate and washed with water, whereby XX-4 was obtained (2.24 g).

(2) In a 50 ml reaction vessel, 1.0 g (3.8 mmol) of XX-4 was dissolved in 9 ml of DMF. 0.167 g (4.18 mmol) of sodium hydride (60%) was added to the solution under a nitrogen stream, and then stirred at room temperature for 1 hour. To the solution, 0.54 ml (4.56 mmol) of benzyl bromide was added dropwise, and then stirred at room temperature for 3 hours. The reaction solution was concentrated under reduced pressure, and then isolated and purified by silica gel chromatography (Mobile phase: Hexane/Ethyl acetate=5/1), whereby XX-5 was obtained (0.99 g).

(3) In a 50 mL reaction vessel, 0.99 g (2.80 mmol) of XX-5 and 364 mg (1.0 mmol) of XX-6 were mixed with a toluene/ethanol/distilled water (6 ml/3 ml/6 ml) mixed solvent, and then dissolved oxygen was removed with nitrogen. Subsequently, 13.7 mg (0.015 mmol) of $Pd_2(dba)_3$, 28.6 mg (0.060 mmol) of 2-dicyclohexyl phosphine-2',4',6'-triisopropyl biphenyl (X-Phos), and 882 mg (2.5 mmol) of cesium carbonate were added under a nitrogen atmosphere, and then subjected to heating reaction at 90° C. for 7 hours. The reaction solution was cooled to room temperature, concentrated under reduced pressure, and then isolated and purified by silica gel chromatography (Mobile phase: Hexane/Ethyl acetate=1/1), whereby A-14 of light yellow solid powder was obtained (170 mg).

656 which is $M^+$ of this compound was confirmed by MALDI-MS measurement.

Example 1 and Comparative Example 1

Spectral Spectrum of Mixed Solution of Anodic/Cathodic EC Compounds

First, Exemplary Compound A-6 as an anodic EC compound and Exemplary Compound C-10 as a cathodic EC compound each were individually dissolved in acetonitrile (15 mM). The solutions were measured for the absorption spectrum in a neutral state (decoloration state) using an ultraviolet visible light spectrophotometer (manufactured by Jasco Corp., V-560).

Figure 3:
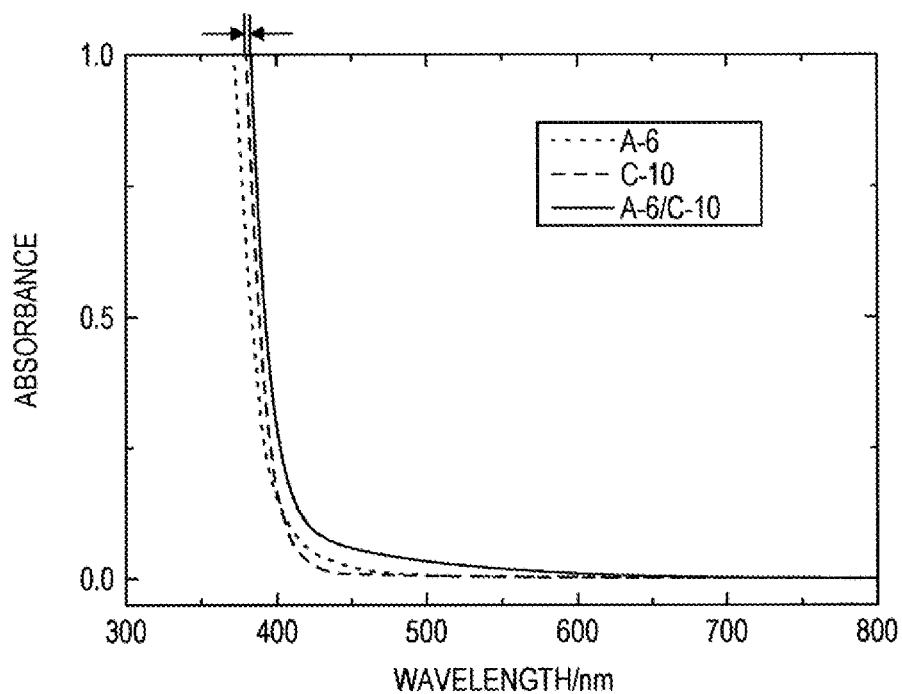
FIG. 3 is a view showing the absorption spectrum in Example 1 of the present invention.

Next, both Compound A-6 and Compound C-10 were mixed and dissolved in acetonitrile (15 mM each), the absorption spectrum of the mixed solution was similarly measured, and then the results of comparing the absorption spectrum with the absorption spectra when dissolving each of the compounds are shown in FIG. 3. Although the absorption spectrum in mixing is shifted to the long wavelength side as compared with the absorption spectra when dissolving each of the compounds, the wavelength shift amount to the long wavelength side when the absorbance is 1 is shown in Table 1.

Figure 4:
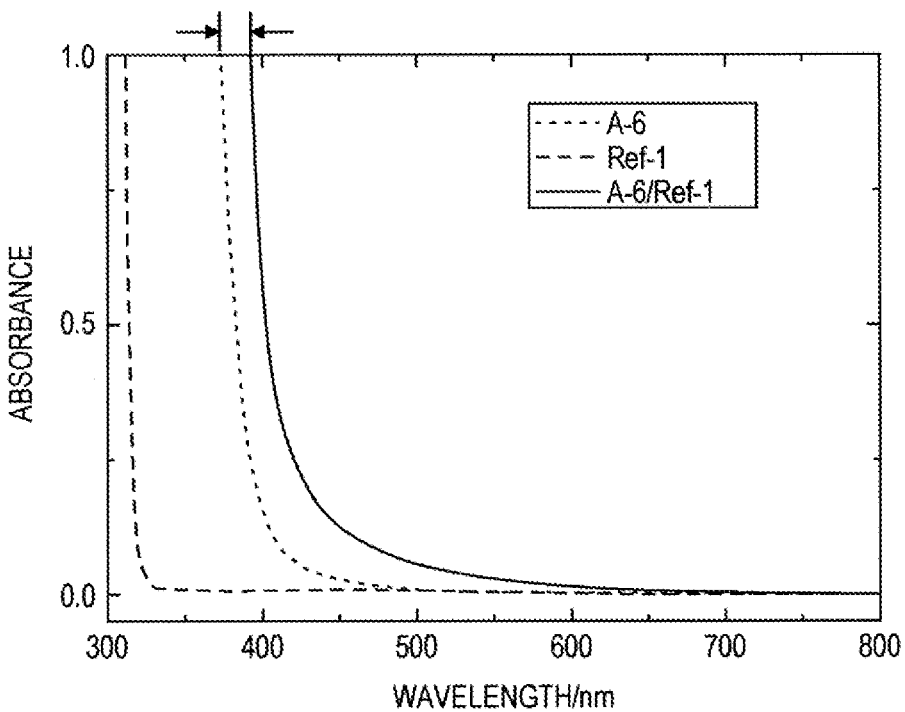
FIG. 4 is a view showing the absorption spectrum in Comparative Example 1 of the present invention.

Furthermore, as a comparative example, the absorption spectrum when mixing an EC compound (diethyl viologen) Ref-1 known as a cathodic compound (the following structural formula) and Anodic EC Compound A-6 is shown in FIG. 4 and the wavelength shift amount to the long wavelength side when the absorbance is 1 is shown in Table 1.

[Chem. 31]

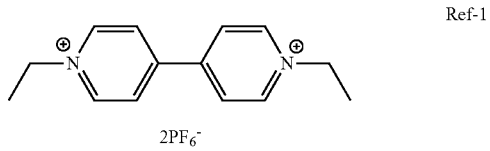

Ref-1

$2PF_6^-$

TABLE 1

| | Anodic EC compound No. | Cathodic EC compound No. | Wavelength shift amount (nm) |
|---|---|---|---|
| Ex. 1 | A-6 | C-10 | 3 |
| Comp. Ex. 1 | A-6 | Ref-1 | 20 |
| Ex. 2 | A-6 | C-5 | 1 |
| Ex. 3 | A-6 | C-6 | 1 |
| Ex. 4 | A-6 | C-14 | 2 |
| Ex. 5 | A-6 | C-1 | 4.5 |

In Comparative Example 1, the absorption spectrum when mixing Anodic EC compound A-6 and Cathodic EC compound Ref-1 was greatly shifted to the long wavelength side, i.e., 20 nm shift, from the absorption spectra of the solutions when dissolving each of the compounds. On the other hand, with respect to the absorption spectrum when mixing Anodic EC compound A-6 and Cathodic EC compound C-10 in Example 1, the shift amount to the long wavelength side from the absorption spectra of the solutions when dissolving each of the compounds was as small as 3 nm.

This is considered that Cathodic EC compound Ref-1 does not have a bulky substituent and does not have steric hindrance in Comparative Example 1, and therefore the wavelength shift amount to the long wavelength side becomes large. This is because the CT interaction is large in Anodic EC compound A-6 and Cathodic EC compound Ref-1. On the other hand, in the mixed solution containing Anodic EC compound A-6 and Cathodic EC compound C-10 according to an aspect of the present invention, a bulky substituent is introduced into both the compounds, and therefore the CT interaction of a thiophene part and a viologen part is greatly reduced. As a result, it is considered that, as compared with the case of dissolving each of the compounds, the spectral change amount is small.

Example 2

A mixed solution was produced in the same manner as in Example 1, except using Exemplary Compound C-5 as a cathodic EC compound, and then the wavelength shift amount was calculated from an absorption spectrum thereof. The result was shown in Table 1.

Example 3

A mixed solution was produced in the same manner as in Example 1, except using Exemplary Compound C-6 as a cathodic EC compound, and then the wavelength shift amount was calculated from an absorption spectrum thereof. The result was shown in Table 1.

Example 4

A mixed solution was produced in the same manner as in Example 1, except using Exemplary Compound C-14 as a cathodic EC compound, and then the wavelength shift amount was calculated from an absorption spectrum thereof. The result was shown in Table 1.

Example 5

A mixed solution was produced in the same manner as in Example 1, except using Exemplary Compound C-1 as a cathodic EC compound, and then the wavelength shift amount was calculated from an absorption spectrum thereof. The result was shown in Table 1.

Example 6 and Comparative Example 2

A mixed solution was produced in the same manner as in Example 1, except using Exemplary Compound A-21 as an anodic EC compound and Exemplary Compound C-14 as a cathodic EC compound, and then the wavelength shift amount was calculated from a comparison between an absorption spectrum of the mixed solution and the absorption spectra of solutions containing each of the compounds. The result was shown in Table 2.

Moreover, as a comparative example, the wavelength shift amount when mixing an EC compound (5,10-dihydro-5,10-dimethyl phenazine) Ref-2 (the following structural formula) known as an anodic compound and Cathodic EC compound C-14 is shown in Table 2.

[Chem. 32]

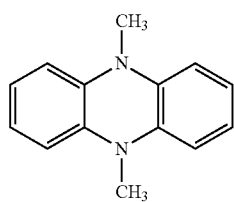

Ref-2

TABLE 2

| | Anodic EC compound No. | Cathodic EC compound No. | Wavelength shift amount (nm) |
|---|---|---|---|
| Ex. 6 | A-21 | C-14 | 2 |
| Comp. Ex. 2 | Ref-2 | C-14 | 74 |
| Ex. 7 | A-21 | C-10 | 4.5 |
| Ex. 8 | B-11 | C-6 | 1.5 |
| Ex. 9 | A-14 | C-6 | 7 |
| Ex. 10 | B-4 | C-5 | 1 |

In Comparative Example 2, Ref-2 which does not have a bulky substituent was used as an anodic EC compound. Therefore, in the absorption spectrum of the solution obtained by mixing C-14 having a bulky substituent with a cathodic compound, remarkable absorption shift to the long wavelength side, i.e., 74 nm shift, from the absorption spectra of the solutions when dissolving each of the compounds was observed. On the other hand, as shown in Example 6, the shift amount to the long wavelength side of the absorption spectrum when mixing Compound A-21 and Compound C-10 was as small as 2 nm as compared with the absorption spectra of solutions when dissolving each of the compounds.

These results are considered to show that, when both the anodic EC compound and the cathodic EC compound have a bulky substituent, the shift amount to the long wavelength side is small, and therefore the CT interaction of a thiophene part and a viologen part is greatly reduced and the transparency is maintained.

Example 7

A mixed solution was produced in the same manner as in Example 6, except using Exemplary Compound C-10 as a cathodic EC compound, and then the wavelength shift amount was calculated from an absorption spectrum thereof. The result was shown in Table 2.

Example 8

A mixed solution was produced in the same manner as in Example 6, except using Exemplary Compound B-11 as an anodic EC compound and C-6 as a cathodic EC compound, and then the wavelength shift amount was calculated from an absorption spectrum thereof. The result was shown in Table 2.

Example 9

A mixed solution was produced in the same manner as in Example 6, except using Exemplary Compound A-14 as an anodic EC compound and C-6 as a cathodic EC compound, and then the wavelength shift amount was calculated from an absorption spectrum thereof. The result was shown in Table 2.

Example 10

A mixed solution was produced in the same manner as in Example 6, except using Exemplary Compound B-4 as an anodic EC compound and C-5 as a cathodic EC compound, and then the wavelength shift amount was calculated from an absorption spectrum thereof. The result was shown in Table 2.

In Examples 1 to 10, since EC compounds having a bulky substituent configuring the EC composition according to an aspect of the present invention were used for both the anodic/cathodic EC compounds, the CT interaction was suppressed. As a result, the shift amount to the long wavelength side is small, and thus it was suggested that Examples were effective for maintaining transparency as compared with Comparative Examples.

Example 11

Production and Property Evaluation of Electrochromic Element

An electrochromic composition was prepared in which Exemplary Compound B-21 as an anodic EC compound and Exemplary Compound C-14 as a cathodic EC compound each having a concentration of 20.0 mM were dissolved in propylene carbonate.

Subsequently, an insulating layer (SiO$_2$) was formed on the periphery of a glass substrate with transparent conductive film (FTO) (lower electrode) while leaving an opening portion which specifies a colored/decolored region. A PET film (Melinex S, manufactured by Teijin DuPont Films Japan Limited, 50 μm thickness) which specifies a substrate interval was maintained by a glass substrate with transparent electrode film (upper electrode). Then, the periphery of an element was sealed with epoxy adhesive while leaving an opening portion for injecting an EC medium to produce an empty cell with injection port.

Next, the prepared EC composition was injected from the element opening portion described above by a vacuum injection method, the opening portion was similarly sealed with epoxy adhesive as in the periphery of the opening portion, whereby as EC element was obtained.

The EC element immediately after the production exhibited a transmittance of 80% or more over the entire visible light region, was free from visible light absorption resulting from the CT interaction, and had high transparency.

When a voltage of 1.5 V was applied to this element, absorption (λmax=686 nm) caused by an oxidation species of Anodic EC material B-21 and absorption (λmax=607 nm) caused by a reduction species of Cathodic EC material C-14 were exhibited, so that the element was colored.

Figure 5:
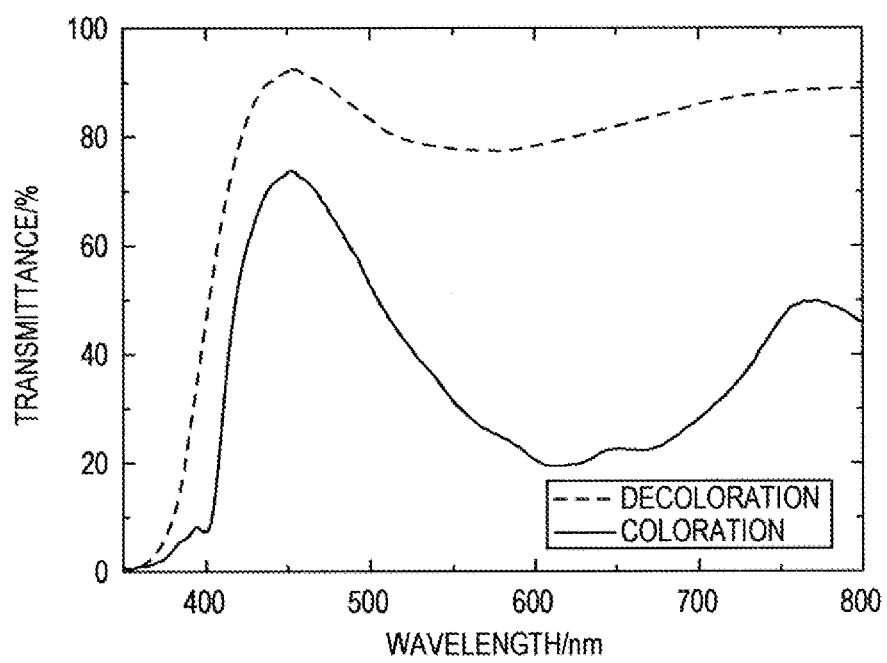
FIG. 5 is a view showing the transmittance spectrum in coloration/decoloration of an electrochromic element in Example 11 of the present invention.

Furthermore, when 0 V was applied, reversible coloration/decoloration was exhibited. The transmittance changes in coloring and in decoloration to this voltage application were shown in FIG. 5.

Thus, it was confirmed that the EC element containing the electrochromic composition according to an aspect of the present invention does not show light absorption in a visible light region in decoloration, has high transparency, and exhibits an outstanding electrochromic property.

As described above, the present invention can provide the EC element containing the EC composition which does not exhibit light absorption based on CT interaction in a visible light region in decoloration and can realize high transparency.

Since the EC composition according to an aspect of the present invention and the EC element having the same have high transparency which does not allow light absorption in a visible light region in decoloration, the EC composition and the EC element can be used for an optical filter, a lens unit, an imaging device, and the like. The present invention can provide an electrochromic composition in which the CT light absorption is suppressed and which has high colorless transparency in decoloration and an electrochromic element having the same.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

REFERENCE SIGNS LIST

10 Transparent substrate
11 Transparent electrode
12 EC composition
13 Spacer
21 3,4-ethylene dioxythiophene part
22 Phenyl Group in which isopropoxy group and methoxy group are replaced

The invention claimed is:
1. An electrochromic composition comprising:
an anodic electrochromic compound; and
a cathodic electrochromic compound,
wherein the anodic electrochromic compound is represented by General Formula [1] and the cathodic electrochromic compound is represented by General Formula [2],

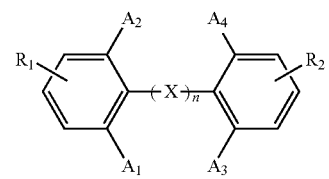

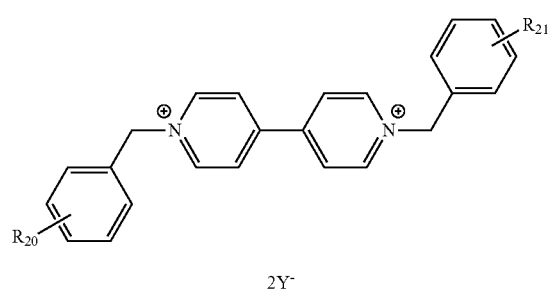

wherein, in General Formula [1], $A_1$ to $A_4$ each independently represent a substituent selected from alkyl groups in which the number of carbon atoms is 1 or more and 20 or less, alkoxy groups in which the number of carbon atoms is 1 or more and 20 or less, and aryl groups which optionally have a substituent,
wherein, when the aryl group has a substituent, the substituent is at least any one of alkyl groups in which the number of carbon atoms is 1 or more and 8 or less or alkoxy groups in which the number of carbon atoms is 1 or more and 8 or less,
wherein $R_1$ and $R_2$ each are independently selected from hydrogen atoms or substituents, the substituents represented by $R_1$ and $R_2$ above each are at least any one of halogen atoms, alkyl groups in which the number of carbon atoms is 1 or more and 20 or less, alkoxy groups in which the number of carbon atoms is 1 or more and 20 or less, alkyl ester groups in which the number of carbon atoms is 1 or more and 20 or less, aryl groups which optionally have a substituent, amino groups which optionally have a substituent, or cyano groups, and two or more $R_1$s and $R_2$s optionally being present,
wherein n is an integer of 1 to 5,
wherein, in General Formula [2], $R_{20}$ and $R_{21}$ each are independently selected from hydrogen atoms or substituents, the substituents represented by $R_{20}$ and $R_{21}$ each are at least any one selected from halogen atoms, alkyl groups in which the number of carbon atoms is 1 or more and 20 or less, alkoxy groups in which the number of carbon atoms is 1 or more and 20 or less, alkyl ester groups in which the number of carbon atoms is 1 or more and 20 or less, acyl groups in which the number of carbon atoms is 1 or more and 20 or less, aryl groups which optionally have a substituent, amino groups which optionally have a substituent, or cyano groups, two or more $R_{20}$s and $R_{21}$s optionally being present, and $Y^-$ represents an anion, wherein X shown in Formula [1], is a structure of any one of General Formulae [3] to [5], in which when n is 2 or more, a plurality of Xs each are independently selected from the following general formulae [3] to [5],

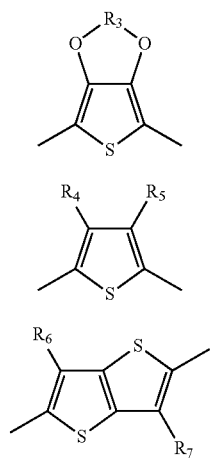

wherein, in General Formula [3], $R_3$ represents an alkylene group in which the number of carbon atoms is 1 or more and 20 or less and which optionally be branched, and wherein, in General Formula [4] and [5], $R_4$ to $R_7$ each represent a hydrogen atom or a substituent, and the substituents represented by $R_4$ to $R_7$ above each are at least any one of halogen atoms, alkyl groups in which the number of carbon atoms is 1 or more and 20 or less, alkoxy groups in which the number of carbon atoms is 1 or more and 20 or less, aryl groups which optionally have a substituent, alkyl ester groups in which the number of carbon atoms is 1 or more and 20 or less, amino groups which optionally have a substituent, or cyano groups.

2. The electrochromic composition according to claim 1, wherein at least either one of $A_1$ or $A_2$ is an alkoxy group in which the number of carbon atoms is 1 or more and 20 or less.

3. The electrochromic composition according to claim 1, wherein at least either one of $A_3$ or $A_4$ is an alkoxy group in which the number of carbon atoms is 1 or more and 20 or less.

4. The electrochromic composition according to claim 1, wherein the alkoxy group represented by at least either one of $A_1$ or $A_2$ is a methoxy group or an isopropoxy group, and the alkoxy group represented by at least either one of $A_3$ or $A_4$ is a methoxy group or an isopropoxy group.

5. The electrochromic composition according to claim 1, wherein $R_{20}$ and $R_{21}$ above are electron withdrawing substituents.

6. The electrochromic composition according to claim 5, wherein $R_{20}$ and $R_{21}$ above each are any one of a tert-butyl group, a trifluoromethyl group, a methoxy group, a benzyloxy group, a methyl ester group, or a cyano group.

7. The electrochromic composition according to claim 1, wherein a weight ratio of the electrochromic compound represented by General Formula [1] is 10% by mol or more and 90% by mol or less when a total of the electrochromic compound represented by General Formula [1] and the electrochromic compound represented by General Formula [2] is 100% by mol.

8. The electrochromic composition according to claim 1 comprising a third electrochromic compound which is different from the electrochromic compound represented by General Formula [1] and the electrochromic compound represented by General Formula [2].

9. The electrochromic composition according to claim 1 further comprising a solvent and an electrolyte.

10. The electrochromic composition according to claim 9, wherein a concentration of the electrolyte is larger than 0 mol/l and 10 mol/l or less based on the solvent.

11. An electrochromic element comprising:
a pair of electrodes; and an electrochromic layer disposed between the pair of electrodes, wherein the electrochromic layer has the electrochromic composition according to claim 1.

12. An optical filter comprising:
the electrochromic element according to claim 11; and
an active element connected to the electrochromic element.

13. A lens unit comprising:
the optical filter according to claim 12; and
an imaging optical system having a plurality of lenses.

14. An imaging device comprising:
the optical filter according to claim 12;
an imaging optical system; and
an image pickup device which performs imaging through the optical filter.

15. An imaging device, which is an imaging device to which an imaging optical system can be attached, the imaging device comprising:
the optical filter according to claim 12; and
an image pickup device which receives light passing through the optical filter.

16. A window material comprising:
a pair of transparent substrates; and
the electrochromic element according to claim 11.

* * * * *